(12) United States Patent
Aygun et al.

(10) Patent No.: US 8,362,229 B2
(45) Date of Patent: Jan. 29, 2013

(54) TANDEM SIRNAS

(75) Inventors: Huseyin Aygun, Frankfurt am Main (DE); Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 594 days.

(21) Appl. No.: 11/704,600

(22) Filed: Feb. 8, 2007

(65) Prior Publication Data

US 2008/0293655 A1 Nov. 27, 2008

Related U.S. Application Data

(60) Provisional application No. 60/771,238, filed on Feb. 8, 2006.

(51) Int. Cl.
*C07H 21/04* (2006.01)
*C07H 21/02* (2006.01)

(52) U.S. Cl. .................. 536/24.5; 536/23.1; 536/24.2

(58) Field of Classification Search .................. None
See application file for complete search history.

(56) References Cited

U.S. PATENT DOCUMENTS

| | | | |
|---|---|---|---|
| 7,056,704 B2 | 6/2006 | Tuschl et al. | |
| 7,078,196 B2 | 7/2006 | Tuschl et al. | |
| 7,452,987 B2 | 11/2008 | Giese et al. | |
| 7,459,547 B2 | 12/2008 | Zamore et al. | |
| 2003/0084471 A1 | 5/2003 | Beach et al. | |
| 2004/0014956 A1 | 1/2004 | Woolf et al. | |
| 2004/0053876 A1 | 3/2004 | Turner et al. | |
| 2004/0054155 A1 | 3/2004 | Woolf et al. | |
| 2005/0037988 A1 | 2/2005 | Zamore et al. | |
| 2005/0282188 A1* | 12/2005 | Haeberli et al. | 435/6 |
| 2006/0025366 A1 | 2/2006 | MacLachlan et al. | |
| 2007/0032441 A1 | 2/2007 | McSwiggen et al. | |

FOREIGN PATENT DOCUMENTS

| | | |
|---|---|---|
| WO | WO 03/070918 A2 | 8/2003 |
| WO | WO 03/070918 A3 | 8/2003 |
| WO | WO 2004/044135 A2 | 5/2004 |
| WO | WO 2004/044135 A3 | 5/2004 |
| WO | WO 2009/001359 A2 | 12/2008 |
| WO | WO 2009/001359 A3 | 12/2008 |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Niittymaki et al., Preparation of Azacrown-Functionalized 2'-O-Methyl Oligoribonucleotides, Potential Artificial RNases, 2004, Bioconjugate Chem., 15, pp. 174-184.*
Mokhir et al., Synthesis and monitored selection of nucleotide surrogates for binding T:A base pairs in homopurine-homopyrimidine DNA triple helices, 2001, Nucleic Acids Research, vol. 29, No. 17, pp. 3674-3684.*
International Search Report issued by the International Searching Authority (ISA/US) on Dec. 12, 2008 in connection with International Application No. PCT/IL07/00184.
Written Opinion of the International Searching Authority (ISA/US) issued on Dec. 12, 2008 in connection with International Application No. PCT/IL07/00184.
International Preliminary Report on Patentability issued by the International Search Authority (ISA/US) Issued on Mar. 10, 2009 in connection with International Application PCT/IL07/00184.
Amarzguioui M. et al. (2003) Tolerance for mutations and chemical modifications in a siRNA. *Nucleic Acids Res.* 31(2) : 589-95.
Braasch D.A. et al. (2003) RNA interference in mammalian cells by chemically-modified RNA. *Biochemistry*, 42 : 7967-7975.
Caplen et al. (2001) Specific inhibition of gene expression by small double-stranded RNAs in invertebrate and vertebrate systems. *Proc Natl Acad Sci*, 98:9742.
Chalk AM, et al. (2004) Improved and automated prediction of effective siRNA. *Biochem. Biophys. Res. Commun.* Jun. 18; 319(1): 264-274.
Czauderna F. et al. (2003) -Structural variations and stabilizing modifications of synthetic siRNAs in mammalian cells. *Nucleic Acids Res.* 31(11): 2705-16.
Elbashir S.M. et al. (2001) Functional anatomy of siRNAs for demiating efficient RNAi in *Drosophila melanogaster* embryo lysate. *Embo J.* 20(23): 6877-88.
Elbashir SM et al (2001) RNA interference is mediated by 21-and 22-nucleotide RNAs. *Genes Dev.*, 15, 188-200.
Elbashir SM et al. (2001) Duplexes 'Of 21-nucleotide RNAs mediate RNA interference in cultured mammalian cells. *Nature* 411:494-498.
Fire et al, (1998), Potent and specific genetic interference by double-stranded RNA in *Caenorhabditis elegans*. *Nature* 391, 806-811.
Hannon GG. (2002) "RNA Interference" *Nature* 418:244-251.
Prakash T.P. et al. (2005) Positional effect of chemical modifications on short interference RNA activity in mammalian cells. *J. Med Chem.* 48(13) 4247-53.
Extended European Search Report and Search Opinion issued by the European Patent Office on Oct. 2, 2009, in connection with European Application No. 07706127.
Sioud M, et al., (2004), Potential design rules and enzymatic synthesis of siRNAs, *Methods Mol Biol.*; 252:457-69.
Sep. 7, 2010 Communication pursuant to Article 94(3) EPC issued by the European Patent Office in connection with EP 07706127.3.
Amended claims and support table filed Jan. 5, 2010 in connection with European Patent Application 07706127.3.

*Primary Examiner* — Amy Bowman
(74) *Attorney, Agent, or Firm* — John P. White; Cooper & Dunham LLP

(57) ABSTRACT

The present invention provides novel molecules, compositions, methods and uses for treating microvascular disorders, eye diseases and respiratory conditions based upon inhibition of two or more target genes.

25 Claims, 17 Drawing Sheets

Figure 1
a)
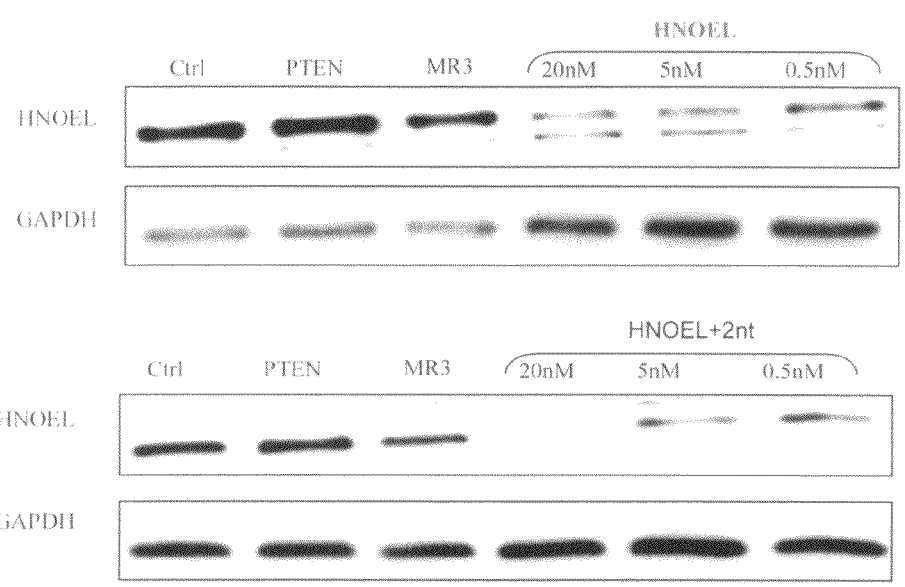
b)
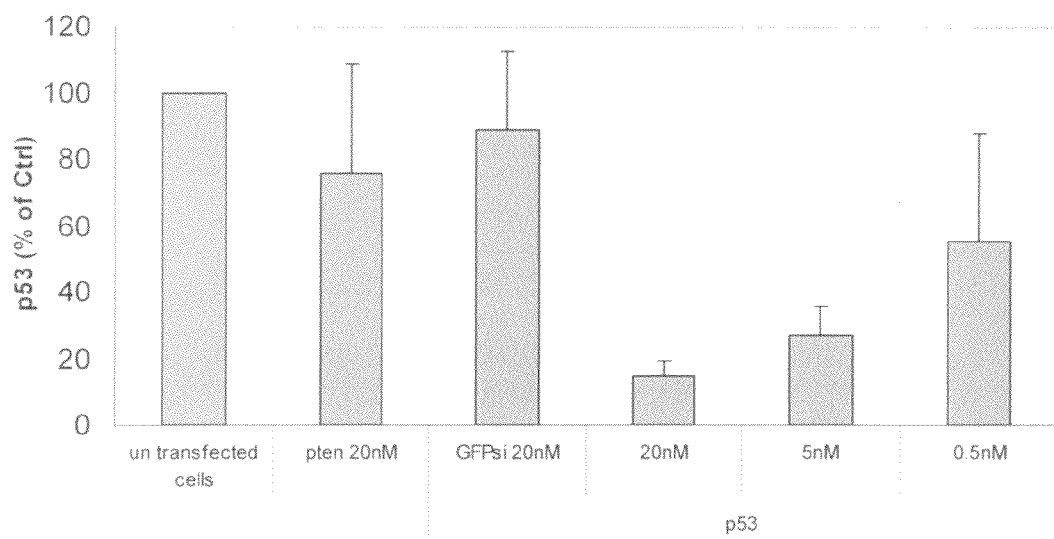

a)

Figure 6 – gapped RNAstar variants
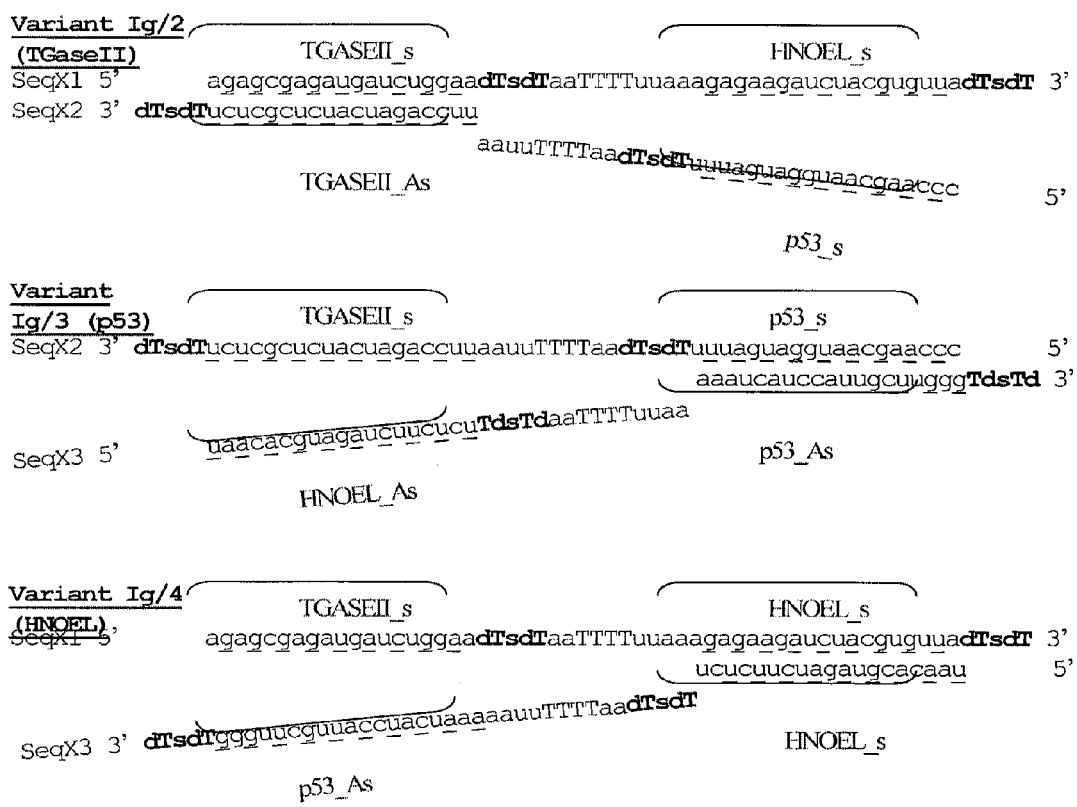

Figure 6 - continued
Variant Ig/5
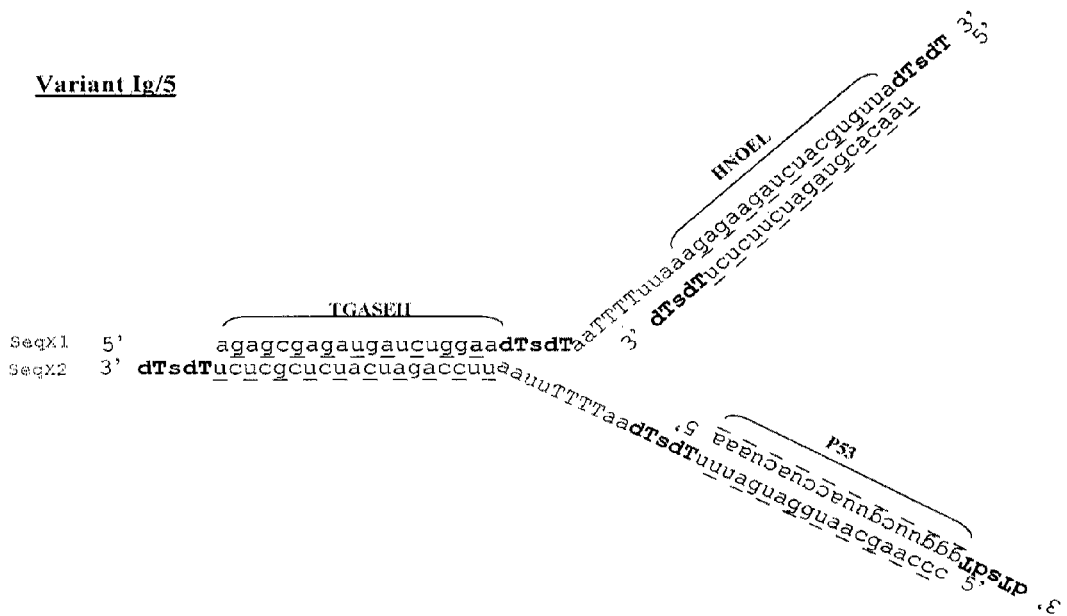

Figure 6 - continued
Variant Ig/6
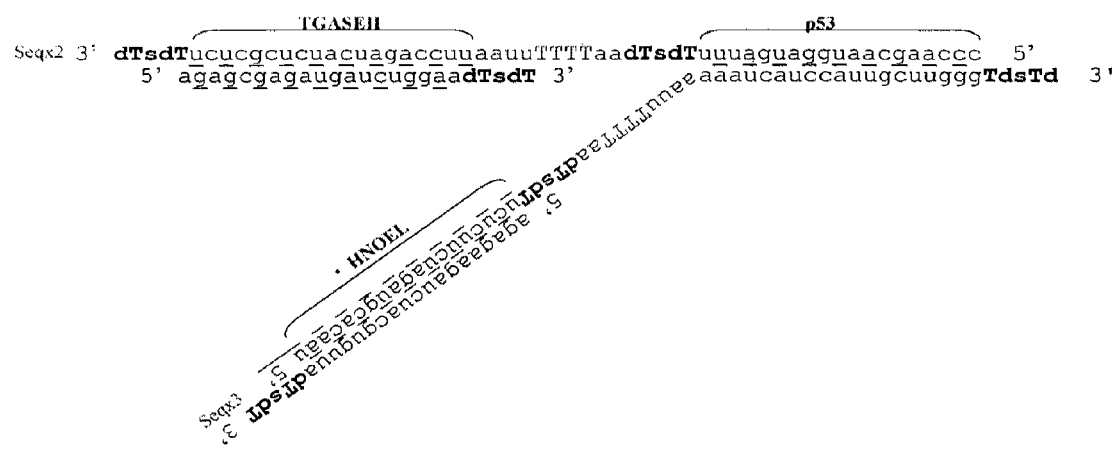

Figure 6 - continued
Variant Ig/7
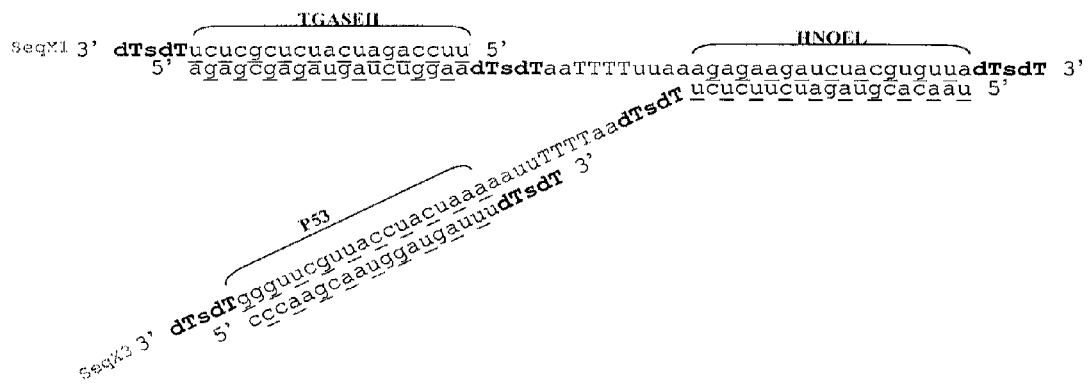

Exemplary structure of RNAstar

A = linker A;
B = linker B;
C = linker C.

A) Western blot analysis of HNOEL expression in 293 cells expressing exogenous human HNOEL cDNA, 72h following gapped RNAstar transfection

Figure 8 – Continued
B) Western blot analysis of TGASEII expression in NRK49 cells expressing exogenous rat TGASEII cDNA, 72h following gapped RNAstar transfection
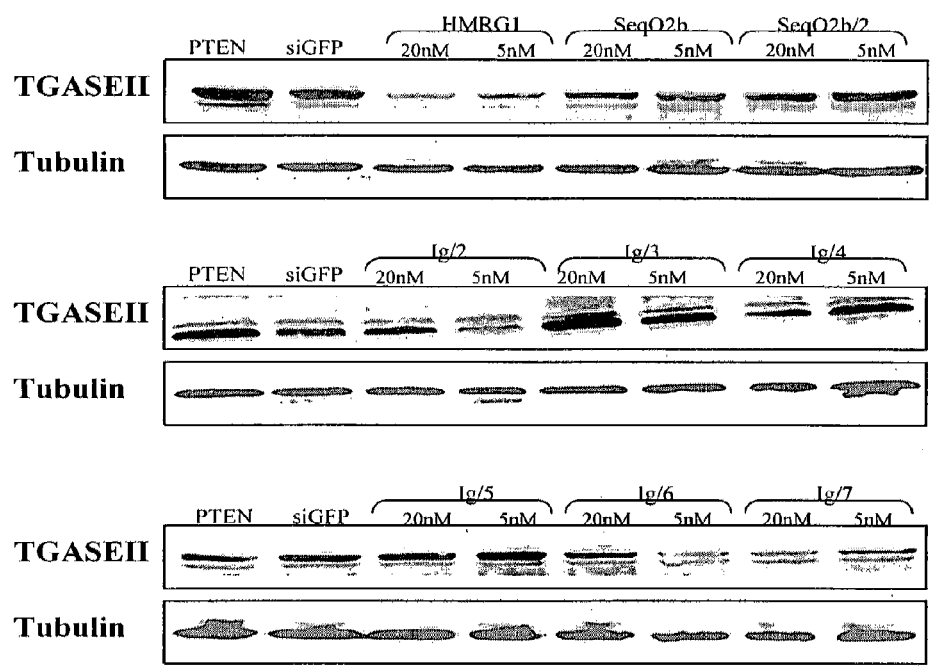

Figure 8 – continued
C) Western blot analysis of p53 expression in 5Fu treated HCT116 cells, 72h following gapped RNAstar transfection
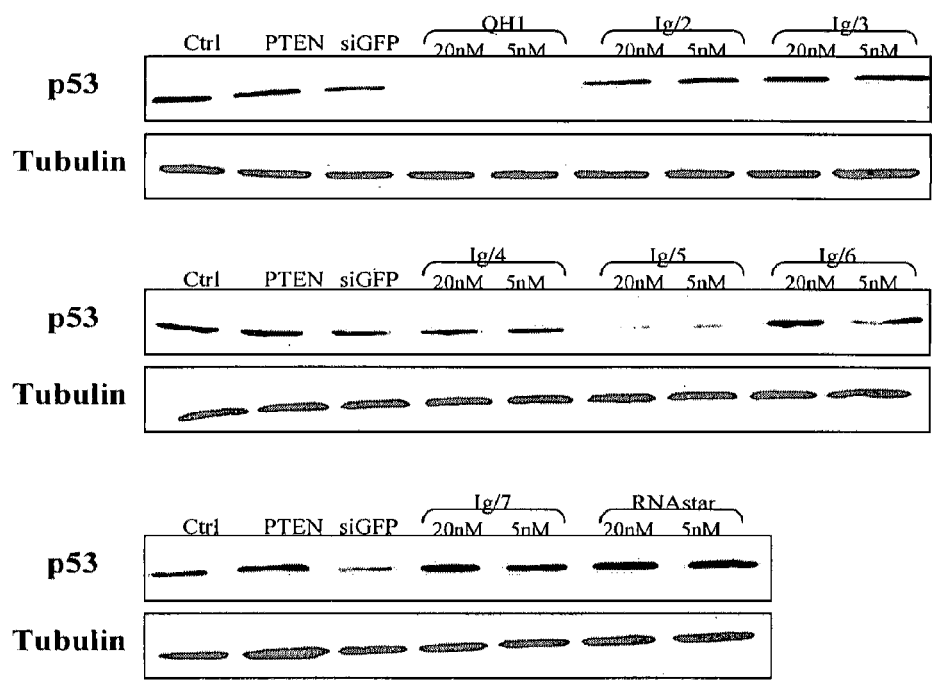

TANDEM SIRNAS

PRIORITY

This application claims the benefit of U.S. Provisional Application No. 60/771,238, filed on Feb. 8, 2006, the contents of which are hereby incorporated by reference in their entirety into this application.

FIELD OF THE INVENTION

The present invention relates to siRNA molecules of a novel design and structure, that are capable of inhibiting two or more genes, optionally simultaneously. These novel siRNAs may be used as drugs to treat a variety of diseases and indications.

BACKGROUND OF THE INVENTION siRNAs and RNA Interference

The present invention relates generally to compounds which down-regulate expression of two or more genes, and particularly to novel small interfering RNAs (siRNAs), and to the use of these novel siRNAs in the treatment of various diseases and medical conditions.

The present invention provides methods and compositions for inhibiting expression of the target genes in vivo. In general, the method includes administering oligoribonucleotides, such as small interfering RNAs (i.e., siRNAs) that are targeted to two or more particular mRNA and hybridize to, or interact with, it under biological conditions (within the cell), or a nucleic acid material that can produce siRNA in a cell, in an amount sufficient to down-regulate expression of two or more target genes by an RNA interference mechanism. Additionally the siRNAs of the invention can be used in vitro as part of a compound screening system to look for small compounds that compete with, or overcome effect of, siRNAs.

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defence mechanism which was activated in response to long dsRNA molecules; see Gil et al. 2000, Apoptosis, 5:107-114. Later it was discovered that synthetic duplexes of 21 nucleotide RNAs could mediate gene specific RNAi in mammalian cells, without the stimulation of the generic antiviral defence mechanisms see Elbashir et al. Nature 2001, 411:494-498 and Caplen et al. Proc Natl Acad Sci 2001, 98:9742-9747. As a result, small interfering RNAs (siRNAs), which are short double-stranded RNAs, have become powerful tools in attempting to understand gene function.

Thus RNA interference (RNAi) refers to the process of sequence-specific post-transcriptional gene silencing in mammals mediated by small interfering RNAs (siRNAs) (Fire et al, 1998, Nature 391, 806) or microRNAs (miRNAs) (Ambros V. Nature 431:7006, 350-355 (2004); and Bartel D P. Cell. 2004 Jan. 23; 116(2):281-97 *MicroRNAs: genomics, biogenesis, mechanism, and function*). The corresponding process in plants is commonly referred to as specific post transcriptional gene silencing or RNA silencing and is also referred to as quelling in fungi. An siRNA is a double-stranded RNA molecule which down-regulates or silences (prevents) the expression of a gene/mRNA of its endogenous or cellular counterpart. RNA interference is based on the ability of dsRNA species to enter a specific protein complex, where it is then targeted to the complementary cellular RNA and specifically degrades it. Thus the RNA interference response features an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). In more detail, longer dsRNAs are digested into short (17-29 bp) dsRNA fragments (also referred to as short inhibitory RNAs—"siRNAs") by type III RNases (DICER, DROSHA, etc., Bernstein et al., Nature, 2001, v. 409, p. 363-6; Lee et al., Nature, 2003, 425, p. 415-9). These fragments and complementary mRNA are recognized by the RISC protein complex. The whole process is culminated by endonuclease cleavage of target mRNA (McManus&Sharp, Nature Rev Genet, 2002, v. 3, p. 737-47; Paddison&Hannon, Curr Opin Mol Ther. 2003 June; 5(3):217-24). For information on these terms and proposed mechanisms, see Bernstein E., Denli A M., Hannon G J: 2001 *The rest is silence*. RNA. 1; 7(11):1509-21; Nishikura K.: 2001 *A short primer on RNAi: RNA-directed RNA polymerase acts as a key catalyst*. Cell. I 116; 107(4):415-8 and PCT publication WO 01/36646 (Glover et al).

The selection and synthesis of siRNA corresponding to known genes has been widely reported; see for example Chalk A M, Wahlestedt C, Sonnhammer E L. 2004 *Improved and automated prediction of effective siRNA* Biochem. Biophys. Res. Commun. June 18; 319(1):264-74; Sioud M, Leirdal M., 2004, *Potential design rules and enzymatic synthesis of siRNAs*, Methods Mol. Biol.; 252:457-69; Levenkova N, Gu Q, Rux J J.: 2004, *Gene specific siRNA selector* Bioinformatics. 112; 20(3):430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 I 9; 32(3):936-48. See also Liu Y, Braasch D A, Nulf C J, Corey D R. *Efficient and isoform-selective inhibition of cellular gene expression by peptide nucleic acids*, Biochemistry, 2004 I 24; 43(7):1921-7. See also PCT publications WO 2004/015107 (Atugen) and WO 02/44321 (Tuschl et al), and also Chiu Y L, Rana T M. *siRNA function in RNAi: a chemical modification analysis*, RNA 2003 September; 9(9):1034-48 and I U.S. Pat. Nos. 5,898,031 and 6,107,094 (Crooke) for production of modified/more stable siRNAs.

Several groups have described the development of DNA-based vectors capable of generating siRNA within cells. The method generally involves transcription of short hairpin RNAs that are efficiently processed to form siRNAs within cells. Paddison et al. *PNAS* 2002, 99:1443-1448; Paddison et al. *Genes & Dev* 2002, 16:948-958; Sui et al. *PNAS* 2002, 8:5515-5520; and Brummelkamp et al. *Science* 2002, 296:550-553. These reports describe methods to generate siRNAs capable of specifically targeting numerous endogenously and exogenously expressed genes.

siRNA has recently been successfully used for inhibition in primates; for further details see Tolentino et al., Retina 24(1) February 2004 1 132-138. Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Bitko et al., "Inhibition of respiratory viruses by nasally administered siRNA", Nat. Med. 2005, 11 (1):50-55). A review of the use of siRNA in medicine was recently published by Barik S. in J. Mol. Med (2005) 83: 764-773). Furthermore, a phase I clinical study with short siRNA molecule that targets the VEGFR1 receptor for the treatment of Age-Related Macular Degeneration (AMD) has been conducted in human patients. The siRNA drug administered by an intravitreal inter-ocular injection was found effective and safe in 14 patients tested after a maximum of 157 days of follow up (Boston Globe Jan. 21, 2005).

Due to the difficulty in identifying and obtaining regulatory approval for chemical drugs for the treatment of diseases, the molecules of the present invention offer an advantage in that they are non-toxic and may be formulated as pharmaceutical compositions for treatment of any disease. Additionally, the molecules of the present invention have the advantage of being able to efficiently treat diseases and conditions in which two or more genes are involved by targeting said genes with one molecule. Another advantage is their lower effective concentration as compared to smaller sized siRNAs. Said combined or tandem structures have the advantage that toxicity and/or off-target effects of each siRNA are reduced.

SUMMARY OF THE INVENTION

The invention provides a novel double stranded oligoribonucleotide. This oligoribonucleotide down-regulates the expression of two or more desired genes by the mechanism of RNA interference. The invention also provides a pharmaceutical composition comprising such oligoribonucleotides, and vectors capable of expressing the ribonucleotides.

The present invention also provides a method of treating a patient suffering from a disease or adverse condition, comprising administering to the patient the oligoribonucleotide typically as a pharmaceutical composition, in a therapeutically effective amount so as to thereby treat the patient.

The present invention also relates to functional nucleic acids comprising a double-stranded or triple-stranded or even multistranded structure, their use for the manufacture of a medicament, a pharmaceutical composition comprising such functional nucleic acids and a method for the treatment of a patient.

BRIEF DESCRIPTION OF THE FIGURES

FIG. 6 presents the structure of different variants of the RNAstar molecule
- [Variant Ig/2 (TGaseII) from top to bottom: SEQ ID NO: 26; SEQ ID NO 27)];
- [Variant Ig/3 (p53) from top to bottom: SEQ ID NO: 27; SEQ ID NO: 28];
- [Variant Ig/4 (HNOEL) from top to bottom: SEQ ID NO: 26; SEQ ID NO: 28];
- [Variant Ig/5 clockwise from top: SEQ ID NO: 26; SEQ ID NO: 41; SEQ ID NO: 43; SEQ ID NO: 27];
- [Variant Ig/6 clockwise from top: SEQ ID NO: 27; SEQ ID NO: 28; SEQ ID NO: 40; SEQ ID NO: 38];
- [Variant Ig/7 clockwise from top: SEQ ID NO: 39; SEQ ID NO: 26; SEQ ID NO: 28; SEQ ID NO: 42];

DETAILED DESCRIPTION OF THE INVENTION

Figure 1C:
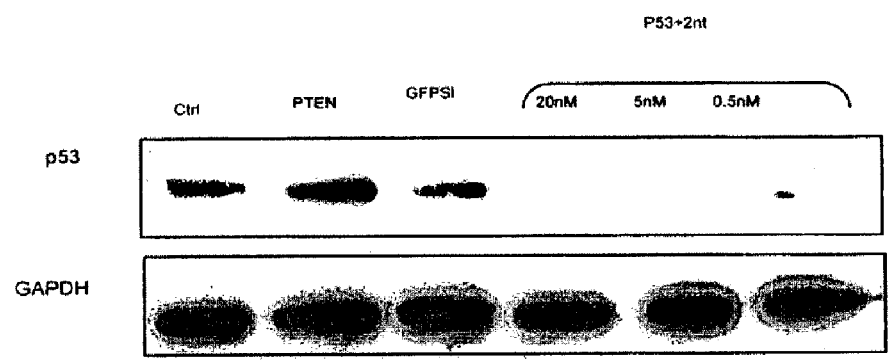
FIGS. 1-5 present the results of various validation experiments which confirm the efficacy of the molecules of the present invention in down-regulation of various genes. Further information concerning these experiments can be found in Example 4.

The present invention relates to oligonucleotides and oligoribonucleotides which possess therapeutic properties. In particular, the present invention discloses tandem oligoribonucleotides which encode two inhibitory RNA molecules such as siRNAs, wherein each siRNA may be specific for a different gene (or wherein both siRNAs are specific for the same gene). Said combined or tandem structures have the advantage that toxicity and/or off-target effects of each siRNA are minimized, while the efficacy is increased. Further, said tandem structures have the additional advantage in that they can treat two separate therapeutic targets and/or diseases with one single molecule. Additionally, the present invention provides for tandem oligonucleotides which encode three siRNAs, as will be described herein. It is also within the scope of the present invention to provide for oligonucleotides which encode three, four or even five inhibitory RNAs which target the same or as many as five different genes.

Thus, in one embodiment, the present invention provides for an oligonucleotide comprising consecutive nucleotides wherein a first segment of such nucleotides encodes a first inhibitory RNA molecule and a second segment of such nucleotides encodes a second inhibitory RNA molecule. Thus, an oligonucleotide which encodes two inhibitory RNA molecules is provided. In a further embodiment, each of the first and the second segment may comprise one strand of a double stranded RNA, and the first and second segments may be joined together by a single stranded RNA linker; a single stranded DNA linker; a linker which comprises a disulfide bond; a linker which comprises a peptide bond; a double stranded RNA linker; a double stranded DNA linker; a linker which comprises a partially single stranded and partially double stranded RNA; or a linker which comprises a partially single stranded and partially double stranded DNA.

Further, the oligonucleotide may comprise modification at the 2' position of one or more sugars, such as 2'Omethyl and/or 2'fluoro substitutions. The 2' modifications may be on alternating nucleotides.

Thus, as detailed above, the oligonucleotide of the present invention may comprise two double stranded RNA sequences linked together by linker, such as a single stranded RNA linker; a single stranded DNA linker; a disulfide linker; a peptide linker; a double stranded RNA linker; a double stranded DNA linker; a partially single stranded and partially double stranded RNA linker; a partially single stranded and partially double stranded DNA linker; or any other kind of cleavable or non-cleavable chemical linker, inter alia. Further, the oligonucleotide may comprise 2'OMethyl or 2'Fluoro or 2'Oallyl or any other 2' modification on preferentially alternate positions. Other stabilizing modifications which do not significantly reduce the enzymatic activity are also possible (e.g., terminal modifications). The backbone of the active part of tandem oligonucleotides preferentially comprises phosphate-D-ribose entities but may also contain thiophosphate-D-ribose entities or any other type of modification. Terminal modifications on the 5' and/or 3' part of the tandem oligonucleotides are also possible. Such terminal modifications may be lipids, peptides, sugars or other molecules.

The oligoribonucleotide of the invention may have one of the following general structures:

1)
5' Oligo1 (sense)      LINKER A Oligo2 (sense)      3'

3' oligo1 (antisense) LINKER B Oligo2 (antisense) 5' wherein either linker A or linker B is present or both linkers A and B are present.

2)
5' oligo1 (antisense) LINKER A Oligo2 (antisense) 3'

3' oligo1 (sense)      LINKER B Oligo2 (sense)      5' wherein either linker A or linker B is present or both linkers A and B are present.

3)
5' oligo1 (sense)      LINKER A Oligo1 (antisense) 3'

3' oligo2 (antisense) LINKER B Oligo2 (sense)      5' wherein either linker A or linker B is present or both linkers A and B are present.

4)
5' oligo1 (antisense) LINKER A Oligo1 (sense)      3'

3' oligo2 (sense)      LINKER B Oligo2 (antisense) 5' wherein either linker A or linker B is present or both linkers A and B are present.

5)
5' oligo1 (sense)   LINKERA   Oligo2 (antisense) 3'

3' oligo2 (sense)   LINKERB   Oligo1 (antisense) 5' wherein either linker A or linker B is present or both linkers A and B are present.

6)
5' oligo1 (antisense) LINKER A   Oligo2 (sense) 3'

3' oligo2 (antisense) LINKER B   Oligo1 (sense) 5' wherein either linker A or linker B is present or both linkers A and B are present.

It is to be understood that in the context of the present invention, the sense and antisense strands of each RNA represented in the tandem molecule can have varying positions in relation with each other, and any sense/antisense conformation with respect to the position of the linker is possible. Linker A and Linker B may each be present or absent, but at least one of Linker A or Linker B must be present. If both present, they may be identical or different. Whether both or only one of Linker A or Linker B are present, they are collectively referred to herein as a "linker". Thus, the linker may covalently join two or more strands of the resultant tandem molecule. For example, each of the above molecules 1-6 is composed of two sense and two antisense strands, and the linker may covalently join two sense strands, two antisense strands, one sense and one antisense strand, two sense strands and one antisense strand, two antisense strands and one sense strand, or two sense and two antisense strands. Molecules with additional strands are also envisaged, and the linker may join any number of strands as specified for the above molecules. In the case of a nucleic acid linker, the resultant tandem molecule may therefore be composed of two continuous strands, or of three strands resulting from one nick or gap in one of the strands, or a multi stranded molecule resulting from two or more nicks or gaps in one or more of the oligos. In the case of a non nucleic acid linker, as will be detailed below, the linker may also join two or more of the strands; in such a case the resultant molecule may have two or more strands, in which the continuous strands contain a non-nucleic acid portion.

Further, the oligoribonucleotides of the present invention may have the following structures:

7)
5' oligo1 (sense)      dTsdTuu      oligo2 (sense)      3'

3' oligo1 (antisense) (gap) dTsdT   oligo2 (antisense) 5' wherein the linker dTsdTuu=5'-2'deoxythymidyl-3'-thiophosphate-5'-2'deoxythymidyl-3'-phosphate-5'-uridyl-3'-phosphate-5'-uridyl-3'-phosphate. Note that the above structure 7 contains a gap.

8)
5' oligo1 (sense)      rUsrU   oligo2 (sense)      3'

3' oligo1 (antisense) (gap)   oligo2 (antisense) 5' wherein the linker rUsrU=a thiophosphate linker: 5'-uridyl-3'-thiophosphate-5'-uridyl-3'-phosphate; the linker may also be substituted with an rUrU linker, i.e., a linker having a phosphate backbone. Note that the above structure 8 contains a gap.

9)
5' oligo1 (sense)      dTsdTaa oligo2 (sense)      3'

3' oligo1 (antisense) aadTsdT oligo2 (antisense) 5' wherein the linker dTsdTaa=aadTsdT=5'-2'deoxythymidyl-3'-thiophosphate-5'-2'deoxythymidyl-3'-phosphate-5'-adenyl-3'-phosphate-5'-adenyl-3'-phosphate. Note that the above structure 9 does not contain a gap.

10)
5' oligo1 (sense)      dTsdT   oligo2 (sense)      3'

3' oligo1 (antisense) dTsdT   oligo2 (antisense) 5' wherein the linker dTsdT=5'-2'deoxythymidyl-3'-thiophosphate-5'-2'deoxythymidyl-3'-phosphate. Note that the above structure 10 does not contain a gap.

11)
5' Oligo1 (sense)      dTsdTuu oligo2 (sense) 3'

3' Oligo1 (antisense) uudTsdT oligo2 (antisense) 5' wherein the linker dTsdTuu=uudTsdT=5'-2'deoxythymidyl-3'-thiophosphate-5'-2'deoxythymidyl-3'-phosphate-5'- uridyl-3'-phosphate-5'-uridyl-3'-phosphate. Note that the above structure 11 does not contain a gap.

12)
(SEQ ID NO: 1)
5' oligo1 (sense)     Y_n    oligo2 (sense) 3'

3' oligo1 (antisense) (gap) oligo2 (antisense) 5' wherein the linker $X_n$=polyRNA (such as, inter alia, poly(5'-adenyl-3'-phosphate—AAAAAAAA) or poly(5'-cytidyl-3'-phosphate-5'-uridyl-3'-phosphate—CUCUCUCU))—a single stranded poly RNA linker wherein n is an integer from 2-50 inclusive, preferable 4-15 inclusive, most preferably 7-8 inclusive. Modified nucleotides or a mixture of nucleotides can also be present in said polyRNA linker. Note that the above structure 12 contains a gap.

13)
(SEQ ID NO: 2)
5' oligo1 (sense)     Y_n    oligo2 (sense) 3'

3' oligo1 (antisense) (gap) oligo2 (antisense) 5' wherein the linker $Y_n$=polyDNA (such as, inter alia, poly(5'-2'deoxythymidyl-3'-phosphate—TTTTTTTT) a single stranded polyDNA linker wherein n is an integer from 2-50 inclusive, preferable 4-15 inclusive, most preferably 7-8 inclusive. Modified nucleotides or a mixture of nucleotides can also be present in said polyDNA linker. Note that the above structure 13 contains a gap.

14)
5' oligo1 (sense)     Y_n    oligo2 (sense) 3'

3' oligo1 (antisense) (gap) oligo2 (antisense) 5'

Wherein the linker —SS—=a linker which comprises a disulfide bond, optionally a bis-hexyl-disulfide linker. Note that the above structure 14 contains a gap.

15)
(SEQ ID NO: 3)
5' oligo1        1-10 a.a.   oligo2 (sense) 3'
(sense)

3' oligo1 (anti- (gap)    oligo2 (antisense) 5'
    sense)

wherein the linker is a linker which comprises a peptide bond, optionally 1-10 amino acid long linker, preferably comprising 4-5 amino acids, optionally X-Gly-Phe-Gly-Y wherein X and Y represent any amino acid. Note that the above structure 15 contains a gap.

Further, with respect to molecules containing any of the linkers as presented in structures 7-15 above, it is to be noted that the order of the sense and antisense strands may be altered, such that any conformation is possible, including but not limited to the general structures 1-7 above comprising any of the linkers of the structures 7-15 above.

In an additional embodiment, the present invention provides for an oligonucleotide as above wherein the oligonucleotide is an oligoribonucleotide which encodes two siRNAs.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove.

This molecule forms a "star"-like structure, and may also be referred to herein as RNAstar.

Said triple-stranded oligonucleotide may be an oligoribonucleotide having the general structure:

5' oligo1 (sense)      LINKERA Oligo2 (sense) 3'

3' oligo1 (antisense)  LINKERB Oligo3 (sense) 5'

3' oligo3 (antisense)  LINKERC oligo2 (antisense) 5'
or

5' oligo1 (sense)      LINKERA Oligo2 (antisense) 3'

3' oligo1 (antisense)  LINKERB Oligo3 (sense) 5'

3' oligo3 (antisense)  LINKERC oligi2 (sense) 5'
or

5' oligo1 (sense)      LINKERA oligo3 (antisense) 3'

3' oligo1 (antisense)  LINKERB oligo2 (sense) 5'

5' oligo3 (sense)      LINKERC oligo2 (antisense) 3' wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different.

Figure 7:
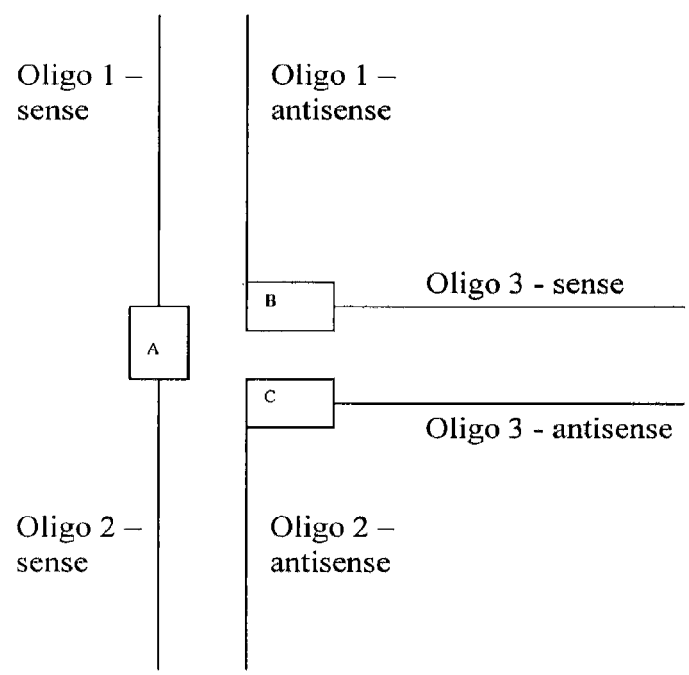
FIG. 7 presents the general structure of an exemplary RNAstar molecule.

Thus, a triple-armed structure is formed, wherein each arm comprises a sense strand and complementary antisense strand. The triple armed structure may be triple stranded, whereby each arm possesses base pairing. An exemplary structure is presented in FIG. 7.

Further, the above triple stranded structure may have a gap instead of a linker in one or more of the strands. Such a molecule with one gap is technically quadruple stranded and not triple stranded; inserting additional gaps or nicks will lead to the molecule having additional strands. Preliminary results obtained by the inventors of the present invention indicate that said gapped molecules are more active in inhibiting certain target genes than the similar but non-gapped molecules. This may also be the case for nicked molecules.

In the context of the present invention, a gap in a nucleic acid means that the molecule is missing one or more nucleotide at the site of the gap, while a nick in a nucleic acid means that there are no missing nucleotides, but rather, there is no phospho-diester bond between 2 adjacent nucleotides at the site of the nick. Any of the molecules of the present invention may contain one or more gap and/or one or more nick.

Examples of the structure of the triple-stranded molecule include the following:

16)
```
5' oligo1 (sense)      HEG   Oligo2 (sense) 3'
3' oligo1 (antisense)  HEG   Oligo3 (sense) 5'
3' oligo3 (antisense)  HEG   oligo2 (antisense) 5'
5' oligo1 (sense)      HEG   oligo3 (antisense) 3'
3' oligo1 (antisense)  HEG   oligo2 (sense) 5'
5' oligo3 (sense)      HEG   oligo2 (antisense) 3'
``` wherein the linker designated HEG is a hexaethylenglycol linker.

17)
```
5' Oligo1 (sense)      Nn  oligo3 (antisense) 3'  (SEQ ID NO: 4)
3' Oligo1 (antisense)  Nn  oligo2 (sense) 5'      (SEQ ID NO: 4)
5' Oligo3 (sense)      Nn  oligo2 (antisense) 3'  (SEQ ID NO: 4)
``` wherein the linker designated Nn is a nucleotide linker, optionally a single stranded nucleotide linker which can be composed of any DNA nucleotides, RNA nucleotides, synthetic nucleotides or any combination thereof (such as, for example, poly(5'-2'deoxythymidyl-3'-phosphate)—a single stranded poly T DNA linker having 4 nucleotides). Further, said linker may be composed of 1-50, typically 1-20 or 2-10 nucleotides, wherein the linker on each of the 3 strands may differ in length.

Additionally, said triple-stranded molecules of the invention may be joined together by any of the linkers disclosed herein. Further, as above in the case of the double stranded molecules, the triple-stranded molecules of the present invention may have a conformation as above except that the order of the sense and antisense strands is altered. Any conformation is possible, as long as at least one sense and one antisense strand are included for each gene target desired for inhibition.

It is to be noted that all of the linkers disclosed herein may have additional recognition sites for cleavage or processing by enzymes or by the chemical environment inside the cell/cell compartments which increase the efficiency of the conversion of said molecules into several separate inhibitory modules.

Further provided by the present invention is a vector comprising any of the oligonucleotide molecules disclosed herein, a vector encoding any of the oligonucleotide molecules disclosed herein, a vector which upon transcription gives rise to any of the oligonucleotide molecules disclosed herein, and a pharmaceutical composition comprising any of the oligonucleotide molecules disclosed herein or any of said vectors comprising or encoding or giving rise to them and a pharmaceutically acceptable carrier.

Said pharmaceutical compositions may be used in the treatment of a variety of diseases and indications and, as discussed herein, they have a particular advantage in that they increase efficacy and minimize side effects, especially when used to treat two separate indications or targets (as opposed to two different drugs). In particular, the pharmaceutical compositions of the present invention can be used to treat a respiratory disorder such as COPD, a microvascular disorder such as acute renal failure (ARF) or diabetic retinopathy and in particular an eye disease such as ocular scarring or macular degeneration.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, anterior ischemic optic neuropathy, optic neuritis (primary or secondary to autoimmune diseases), glaucoma, von Hippel Lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, neuropathies, nephropathies, microvascular diseases of the kidney, and ischemic microvascular conditions, inter alia. Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. All these neovascular conditions may be treated using the compounds and pharmaceutical compositions of the present invention.

"Eye disease" refers to refers to conditions, diseases or syndromes of the eye including but not limited to any conditions involving choroidal neovascularization (CNV), wet and dry AMD, ocular histoplasinosis syndrome, angiod streaks, ruptures in Bruch's membrane, myopic degeneration, ocular tumors, ocular scarring, retinal degenerative diseases and retinal vein occlusion (RVO).

The pharmaceutical composition is in its various embodiments is adapted for administration in various ways. Such administration comprises systemic and local administration as well as oral, subcutaneous, parenteral, intravenous, intraarterial, intramuscular, intraperitonial, intranasal, aerosol and intrategral administration, and administration by inhalation.

It will be acknowledged by those skilled in the art that the amount of the pharmaceutical composition and the respective nucleic acid and vector, respectively, depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but limited to improve the diseased condition or to provide for a more rapid recovery, improvement or elimination of symptoms and other indicators as are selected as appropriate measures by those skilled in the medical arts.

In a preferred embodiment, the pharmaceutical composition according to the present invention may comprise other pharmaceutically active compounds. Preferably, such other pharmaceutically active compounds are selected from the group comprising compounds which allow for uptake intracellular cell delivery, compounds which allow for endosomal release, compounds which allow for, longer circulation time and compounds which allow for targeting of endothelial cells or pathogenic cells. Preferred compounds for endosomal release are chloroquine, and inhibitors of ATP dependent $H^+$ pumps. The pharmaceutical composition is preferably formulated so as to provide for a single dosage administration or a multi-dosage administration. For further information on dosage, formulation and delivery of the compounds of the present invention see Example 7.

"Treating a disease" refers to administering a therapeutic substance effective to ameliorate symptoms associated with a disease, to lessen the severity or cure the disease, or to prevent the disease from occurring.

The term "disease" comprises any illness or adverse condition.

A "therapeutically effective dose" refers to an amount of a pharmaceutical compound or composition which is effective to achieve an improvement in a patient or his physiological systems including, but not limited to, improved survival rate, more rapid recovery, or improvement or elimination of symptoms, and other indicators as are selected as appropriate determining measures by those skilled in the art.

An "inhibitor" is a compound which is capable of inhibiting the activity of a gene or the product of such gene to an extent sufficient to achieve a desired biological or physiological effect. Such inhibitors include substances that affect the transcription or translation of the gene as well as substances that affect the activity of the gene product. Examples of such inhibitors may include, inter alia: polynucleotides such as antisense (AS) fragments, siRNA, or vectors comprising them; polypeptides such as dominant negatives, antibodies, and enzymes; catalytic RNAs such as ribozymes; and chemical molecules with a low molecular weight e.g. a molecular weight below 2000 daltons.

"Expression vector" refers to a vector that has the ability to incorporate and express heterologous DNA fragments in a foreign cell. Many prokaryotic and eukaryotic expression vectors are known and/or commercially available. Selection of appropriate expression vectors is within the knowledge of those having skill in the art.

By "small interfering RNA" (siRNA) is meant an RNA molecule which decreases or silences (prevents) the expression of a gene/mRNA of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs) (Fire et al, 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). For recent information on these terms and proposed mechanisms, see Bernstein E., Denli A M., Hannon G J: *The rest is silence. RNA.* 2001 November; 7(11):1509-21; and Nishikura K.: *A short primer on RNAi: RNA-directed RNA polymerase acts as a key catalyst. Cell.* 2001 Nov. 16; 107(4):415-8.

During recent years, RNAi has emerged as one of the most efficient methods for inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol Ther. 2003 June; 5(3):217-24).

For disclosure on how to design and prepare siRNA to known genes see for example Chalk A M, Wahlestedt C, Sonnhammer E L. *Improved and automated prediction of effective siRNA* Biochem. Biophys. Res. Commun. 2004 Jun. 18; 319(1):264-74; Sioud M, Leirdal M., *Potential design rules and enzymatic synthesis of siRNAs*, Methods Mol Biol. 2004; 252:457-69; Levenkova N, Gu Q, Rux J J.: Gene specific siRNA selector Bioinformatics. 2004 Feb. 12; 20(3): 430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 Feb. 9; 32(3):936-48. See also Liu Y, Braasch D A, Nulf C J, Corey D R. *Efficient and isoform-selective inhibition of cellular gene expression by peptide nucleic acids* Biochemistry, 2004 Feb. 24; 43(7):1921-7. See also PCT publications WO 2004/015107 (Atugen) and WO 02/44321 (Tuschl et al), and also Chiu Y L, Rana T M. siRNA function in RNAi: a chemical modification analysis, RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have been developed. The method generally involves transcription of short hairpin RNAs that are efficiently processed to form siRNAs within cells. Paddison et al. *PNAS* 2002, 99:1443-1448; Paddison et al. *Genes & Dev* 2002, 16:948-958; Sui et al. *PNAS* 2002, 8:5515-5520; and Brummelkamp et al. *Science* 2002, 296:550-553. These reports describe methods to generate siRNAs capable of specifically targeting numerous endogenously and exogenously expressed genes.

For delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 pp 132-138.
siRNAs of the Present Invention
General Specifications of siRNAs of the Present Invention Generally, the siRNAs used in the present invention comprise a ribonucleic acid comprising a double stranded structure, whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, whereby said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides. Further, said first strand and/or said second strand may comprise said plurality of modified nucleotides and may comprises said plurality of groups of modified nucleotides.

The group of modified nucleotides and/or the group of flanking nucleotides may comprise a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

The pattern of modified nucleotides of said first strand may be the same as the pattern of modified nucleotides of said second strand, and may align with the pattern of said second strand. Additionally, the pattern of said first strand may be shifted by one or more nucleotides relative to the pattern of the second strand.

The modifications discussed above may be selected from the group comprising sugar modifications such as amino, fluoro, alkoxy (including LNAs [linked nucleic acids]—which are circularized alkoxy modifications) or alkyl and base modifications such as 5-Alkyl-pyrimidines, 7-Deaza-purines, 8-Alkyl-purines or many other base modifications.

The double stranded structure of the siRNA may be blunt ended, on one or both sides. More specifically, the double stranded structure may be blunt ended on the double stranded structure's side which is defined by the 5'-end of the first strand and the 3'-end of the second strand, or the double stranded structure may be blunt ended on the double stranded structure's side which is defined by at the 3'-end of the first strand and the 5'-end of the second strand. Additionally, at least one of the two strands may have an overhang of at least one nucleotide at the 5'-end; the overhang may consist of at least one deoxyribonucleotide. At least one of the strands may also optionally have an overhang of at least one nucleotide at the 3'-end.

The length of the double-stranded structure of the siRNA is typically from about 17 to 21 and more preferably 18 or 19 bases. Further, the length of said first strand and/or the length of said second strand may independently from each other be selected from the group comprising the ranges of from about 15 to about 23 bases, 17 to 21 bases and 18 or 19 bases. Additionally, the complementarily between said first strand and the target nucleic acid may be perfect, or the duplex formed between the first strand and the target nucleic acid may comprise at least 15 nucleotides wherein there is one mismatch or two mismatches between said first strand and the target nucleic acid forming said double-stranded structure.

In some cases both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides. Each group of modified nucleotides may consist of a single nucleotide and/or each flanking group of nucleotides may consist of a single nucleotide.

Additionally, it is possible that on the first strand the nucleotide forming the flanking group of nucleotides is an unmodified nucleotide which is arranged in a 3' direction relative to the nucleotide forming the group of modified nucleotides, and on the second strand the nucleotide forming the group of modified nucleotides is a modified nucleotide which is arranged in 5' direction relative to the nucleotide forming the flanking group of nucleotides. Further the first strand of the siRNA may comprise eight to twelve, preferably nine to eleven, groups of modified nucleotides, and the second strand may comprise seven to eleven, preferably eight to ten, groups of modified nucleotides.

The first strand and the second strand may be linked by a loop structure, which may be comprised of a non-nucleic acid polymer such as, inter alia, polyethylene glycol. Alternatively, the loop structure may be comprised of a nucleic acid. The loop structure may additionally be comprised of amino acids or PNAs.

Further, the 5'-terminus of the first strand of the siRNA may be linked to the 3'-terminus of the second strand, or the 3'-end of the first strand may be linked to the 5'-terminus of the second strand, said linkage being via a nucleic acid linker typically having a length between 10-2000 nucleobases.

The siRNAs of the present invention, the various possible properties of which are described herein, are linked together by a variety of linkers as described above, such that a molecule which comprises two siRNA moieties is created. Such molecules are novel and may be used to treat a variety of indications, as described herein.

Particular Specifications of siRNAs of the Present Invention

The invention provides a molecule comprising a compound having the structure:

```
5'  (N)_x-Z 3'        (antisense strand) (SEQ ID NO: 5)

3'  Z'-(N')_y 5'      (sense strand)     (SEQ ID NO: 6)
``` wherein each N and N' is a ribonucleotide which may be modified or unmodified in its sugar and/or base and/or backbone and $(N)_x$ and $(N')_y$ is oligomer in which each consecutive N or N' is joined to the next N or N' by a covalent bond;

wherein each of x and y is an integer between 19 and 40; and wherein each of Z and Z' may be present or absent, but if present is dTdT, rUrU, dUdU or rTrT and is covalently attached at the 3' terminus of the strand in which it is present.

In particular, the invention provides the above compound wherein the covalent bond is a phosphodiester bond, wherein x=y or y−1, preferably wherein x=y=19 or 20; or x=20 and y=19; or x=19 and y=20, wherein Z and Z' are both absent, wherein at least one ribonucleotide is modified in its sugar residue at the 2' position, wherein the moiety at the 2' position is methoxy (2'-O-Methyl) wherein alternating ribonucleotides are modified in both the antisense and the sense strands and wherein the ribonucleotides at the 5' and 3' termini of the antisense strand are modified in their sugar residues, and the ribonucleotides at the 5' and 3' termini of the sense strand are unmodified in their sugar residues.

Additionally, stabilizing terminal modifications are also possible, according to the following examples, inter alia:

Example

```
                                           (SEQ ID NO: 7)
(1) agagcgagaugaucuggaa-rUsrU-agagaagaucuacguguua
```

Example

```
                                           (SEQ ID NO: 8)
(2) agagcgagaugaucuggaa-rUsrU-agagaagaucuacguguua
```

Note that s indicates thiophosphate; underlining indicates modification, such as 2'O-methyl.

Further, this aspect provides for a pharmaceutical composition comprising two or more compounds of the above structure covalently or non-covalently linked, preferably by a linker, for the treatment of any disease or condition. Said two compounds may be covalently or non-covalently bound, or joined together by a nucleic acid linker of a length ranging from 2-100, preferably 2-50 or 2-30 nucleotides; or by a non nucleic acid linker such as HEG, diasulfide or a peptide linker. Such siRNA molecules are therefore comprised of a double-stranded nucleic acid structure as described herein. Such tandem siRNA molecules comprising two siRNA sequences would typically be of 38-150 nucleotides in length, more preferably 38 or 40-60 nucleotides in length, and longer accordingly if more than two siRNA sequences are included in the tandem molecule. A longer tandem molecule comprised of two or more longer sequences which encode a molecule comprising siRNA which is produced via internal cellular processing, e.g., long dsRNAs, is also envisaged, as is a tandem molecule encoding two or more shRNAs. Such tandem molecules are also considered to be a part of the present invention.

Said combined or tandem structures have the advantage that toxicity and/or off-target effects of each siRNA are minimized, while the efficacy is increased—all as described herein.

Additionally the siRNA molecule used in the present invention may be an oligoribonucleotide an oligoribonucleotide wherein the dinucleotide dTdT is covalently attached to the 3' terminus, and/or in at least one nucleotide a sugar residue is modified, possibly with a modification comprising a 2'-O-Methyl modification. Further, the 2' OH group may be replaced by a group or moiety selected from the group comprising —$OCH_3$, —$OCH_2CH_3$, —$OCH_2CH_2CH_3$, —O—$CH_2CHCH_2$, —$NH_2$, —O-alkoxy, —O-LNA (linked to the 4' carbon of the sugar) and F. Further, the preferable compounds of the present invention as disclosed above may be phosphorylated or non-phosphorylated.

Additionally, the siRNA used in the present invention may be an oligoribonucleotide wherein in alternating nucleotides modified sugars are located in both strands. Particularly, the oligoribonucleotide may comprise one of the sense strands wherein the sugar is unmodified in the terminal 5' and 3' nucleotides, or one of the antisense strands wherein the sugar is modified in the terminal 5' and 3' nucleotides.

As detailed above, possible modification of the molecules of the present invention include modification of a sugar moiety, optionally at the 2' position, whereby the 2' OH group is replaced by a group or moiety selected from the group comprising —H—$OCH_3$, —$OCH_2CH_3$, —$OCH_2CH_2CH_3$, —O—$CH_2CHCH_2$, —$NH_2$, and —F.

Further possible modifications include modification of the nucleobase moiety and the modification or modified nucleobase may be selected from the group comprising inosine, xanthine, hypoxanthine, 2-aminoadenine, 6-methyl, 2-propyl and other alkyladenines, 5-halo-uracil, 5-halo-cytosine, 5-halo-cytosine, 6-aza-cytosine, 6-aza-thymine, pseudouracil, 4-thio-uracil, 8-halo-adenine, 8-amino-adenine, 8-thiol-adenine, 8-thioalkyl-adenines, 8-hydroxyl-adenine and other 8-substituted adenines, 8-halo-guanines, 8-amino-guanine, 8-thiol-guanine, 8-thioalkyl-guanine, 8-hydroxyl-guanine and other substituted guanines, other aza- and deaza adenines, other aza- and deaza guanines, 5-trifluoromethyl-uracil and 5-trifluoro-cytosine.

In an additional embodiment the modification is a modification of the phosphate moiety, whereby the modified phosphate moiety is selected from the group comprising phosphothioate or lack of a phosphate group.

The tandem molecules of the present invention may comprise siRNAs, synthetic siRNAs, shRNAs and synthetic shRNAs, in addition to other nucleic acid sequences or molecules which encode such molecules or other inhibitory nucleotide molecules. As used herein siRNAs may additionally comprise expression vector derived siRNAs, whereby the expression vector is in a preferred embodiment a virus such as Adenoviruses, Adenoassociated viruses, Herpes viruses and Lentiviruses. As used herein shRNA preferably means short hairpin RNAs. Such shRNA can be made synthetically or can be generated using vector encoded expression systems, preferably using RNA polymerase III promoters.

As used herein with any strategy for the design of tandem molecules, RNAi or any embodiment of RNAi disclosed herein, the term end modification means a chemical entity added to the most 5' or 3' nucleotide of the first and/or second strand. Examples for such end modifications include, but are not limited to, 3' or 5' phosphate, inverted abasic, abasic, amino, fluoro, chloro, bromo, CN, $CF_3$, methoxy, imidazolyl, carboxylate, phosphothioate, $C_1$ to $C_{22}$ and lower alkyl, lipids, sugars and polyaminoacids (i.e. peptides), substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586520 B1 or EP0618925 B1.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications.

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either desoxyribonucleotides or ribonucleotides which do not have a nucleobase moiety. This kind of compound is, among others, described in Sternberger, M., Schmiedeknecht, A., Kretschmer, A., Gebhardt, F., Leenders, F., Czauderna, F., Von Carlowitz, I., Engle, M., Giese, K., Beigelman, L. & Klippel, A. (2002). Antisense Nucleic Acid Drug Dev, 12, 131-43

Further modifications can be related to the nucleobase moiety, the sugar moiety or the phosphate moiety of the individual nucleotide.

Such modification of the nucleobase moiety can be such that the derivatives of adenine, guanine, cytosine and thymidine and uracil, respectively, are modified. Particularly preferred modified nucleobases are selected from the group comprising inosine, xanthine, hypoxanthine, 2-aminoadenine, 6-methyl, 2-propyl and other alkyladenines, 5-halo-uracil, 5-halo-cytosine, 5-halo-cytosine, 6-aza-cytosine, 6-aza-thymine, pseudouracil, 4-thio-uracil, 8-halo-adenine, 8-amino-adenine, 8-thiol-adenine, 8-thioalkyl-adenines, 8-hydroxyl-adenine and other 8-substituted adenines, 8-halo-guanines, 8-amino-guanine, 8-thiol-guanine, 8-thioalkyl-guanine, 8-hydroxyl-guanine and other substituted guanines, other aza- and deaza adenines, other aza- and deaza guanines, 5-trifluoromethyl-uracil and 5-trifluoro-cytosine. In another preferred embodiment, the sugar moiety of the nucleotide is modified, whereby such modification preferably is at the 2' position of the ribose and desoxyribose moiety, respectively, of the nucleotide. More preferably, the 2' OH group is replaced by a group or moiety selected from the group comprising amino, fluoro, alkoxy and alkyl. Preferably, alkoxy is either methoxy or ethoxy. Also preferably alkyl means methyl, ethyl, propyl, isobutyl, butyl and isobutyl. It is even more preferred that, regardless of the type of modification, the nucleotide is preferably a ribonucleotide.

A further form of nucleotides used may be siRNA which is described in international patent application WO 03/070918, inter alia.

It is to be understood that, in the context of the present invention, any of the siRNA molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, can be incorporated into the tandem molecules of the present invention to form additional novel molecules, and can employed in the treatment of the diseases or disorders described herein.

In particular, it is envisaged that a long oligonucleotide (typically about 80-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence. Such a molecule and other similar molecules may encode two, three, four or even five siRNAs which may target one or more genes and function in a manner similar to the other tandem siRNA molecules disclosed herein. Such a molecule will include the linkers disclosed herein.

Any molecules, such as, for example, antisense DNA molecules which comprise the inhibitory sequences disclosed herein (with the appropriate nucleic acid modifications) are particularly desirable and may be used in the same capacity as their corresponding RNAs/siRNAs for all uses and methods disclosed herein.

By the term "antisense" (AS) or "antisense fragment" is meant a polynucleotide fragment (comprising either deoxyribonucleotides, ribonucleotides, synthetic nucleotides or a mixture thereof) having inhibitory antisense activity, said activity causing a decrease in the expression of the endogenous genomic copy of the corresponding gene. The sequence of the AS is designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with the target mRNA, resulting in mRNA degradation (Calabretta et al, 1996: *Antisense strategies in the treatment of leukemias. Semin Oncol.* 23(1). 78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

All analogues of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary nucleic acid—such as a DNA sequence— than a DNA molecule. This observation is attributed to the lack of charge repulsion between the PNA strand and the DNA strand. Other modifications that can be made to oligonucleotides include polymer backbones, cyclic backbones, or acyclic backbones.

By "homolog/homology", as utilized in the present invention, is meant at least about 70%, preferably at least about 75% homology, advantageously at least about 80% homology, more advantageously at least about 90% homology, even more advantageously at least about 95%, e.g., at least about 97%, about 98%, about 99% or even about 100% homology. The invention also comprehends that these nucleotides/oligonucleotides/polynucleotides can be used in the same fashion as the herein or aforementioned polynucleotides and polypeptides.

Alternatively or additionally, "homology", with respect to sequences, can refer to the number of positions with identical nucleotides, divided by the number of nucleotides in the shorter of the two sequences, wherein alignment of the two sequences can be determined in accordance with the Wilbur and Lipman algorithm ((1983) Proc. Natl. Acad. Sci. USA 80:726); for instance, using a window size of 20 nucleotides, a word length of 4 nucleotides, and a gap penalty of 4, computer-assisted analysis and interpretation of the sequence data, including alignment, can be conveniently performed using commercially available programs (e.g., Intelligenetics™ Suite, Intelligenetics Inc., CA). When RNA sequences are said to be similar, or to have a degree of sequence identity or homology with DNA sequences, thymidine (T) in the DNA sequence is considered equal to uracil (U) in the RNA sequence.

RNA sequences within the scope of the invention can be derived from DNA sequences or their complements, by substituting thymidine (T) in the DNA sequence with uracil (U). Additionally or alternatively, amino acid sequence similarity or homology can be determined, for instance, using the BlastP program (Altschul et al., Nucl. Acids Res. 25:3389-3402) and available at NCBI. The following references provide algorithms for comparing the relative identity or homology of amino acid residues of two polypeptides, and additionally, or alternatively, with respect to the foregoing, the teachings in these references can be used for determining percent homology: Smith et al., (1981) Adv. Appl. Math. 2:482-489; Smith et al., (1983) Nucl. Acids Res. 11:2205-2220; Devereux et al., (1984) Nucl. Acids Res. 12:387-395; Feng et al., (1987) J. Molec. Evol. 25:351-360; Higgins et al., (1989) CABIOS 5:151-153; and Thompson et al., (1994) Nucl. Acids Res. 22:4673-4680. "Having at least X % homolgy"—with respect to two amino acid or nucleotide sequences, refers to the percentage of residues that are identical in the two sequences when the sequences are optimally aligned. Thus, 90% amino acid sequence identity means that 90% of the amino acids in two or more optimally aligned polypeptide sequences are identical.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic syntheses: Vol.* 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

The features of the present invention disclosed in the specification, the claims and/or the drawings may both separately and in any combination thereof be material for realizing the invention in various forms thereof.

Example 1

General Materials and methods

If not indicated to the contrary, the following materials and methods were used in Examples 1-5:
Cell Culture The first human cell line, namely HeLa cells (American Type Culture Collection) were cultured as follows: Hela cells (American Type Culture Collection) were cultured as described in Czauderna F et al. (Czauderna, F., Fechtner, M., Aygun, H., Arnold, W., Klippel, A., Giese, K. & Kaufmann, J. (2003). Nucleic Acids Res, 31, 670-82).

The second human cell line was a human keratinozyte cell line which was cultivated as follows: Human keratinocytes were cultured at 37° C. in Dulbecco's modified Eagle medium (DMEM) containing 10% FCS.

The mouse cell line was B16V (American Type Culture Collection) cultured at 37° C. in Dulbecco's modified Eagle medium (DMEM) containing 10% FCS. Culture conditions were as described in Methods Find Exp Clin Pharmacol. 1997 May; 19(4):231-9:

In each case, the cells were subject to the experiments as described herein at a density of about 50,000 cells per well and the double-stranded nucleic acid according to the present invention was added at 20 nM, whereby the double-stranded nucleic acid was complexed using 1 µg/ml of a proprietary lipid as described below.

Induction of Hypoxia-Like Conditions

The cells were treated with CoCl$_2$ for inducing a hypoxia-like condition as follows: siRNA transfections were carried out in 10-cm plates (30-50% confluency) as described by (Czauderna et al., 2003; Kretschmer et al., 2003). Briefly, siRNA were transfected by adding a preformed 10× concentrated complex of GB and lipid in serum-free medium to cells in complete medium. The total transfection volume was 10 ml. The final lipid concentration was 1.0 µg/ml; the final siRNA concentration was 20 nM unless otherwise stated.

Induction of the hypoxic responses was carried out by adding CoCl$_2$ (100 µM) directly to the tissue culture medium 24 h before lysis.

Preparation of Cell Extracts and Immuno Blotting

The preparation of cell extracts and immuno blot analysis were carried out essentially as described by Klippel et al. (Klippel, A., Escobedo, M. A., Wachowicz, M. S., Apell, G., Brown, T. W., Giedlin, M. A., Kavanaugh, W. M. & Williams, L. T., (1998). Mol Cell Biol, 18, 5699-711; Klippel, A., Reinhard, C., Kavanaugh, W. M., Apell, G., Escobedo, M. A. & Williams, L. T. (1996). Mol Cell Biol, 16, 4117-27). Polyclonal antibodies against full length RTP801 were generated by immunising rabbits with recombinant RTP801 protein producing bacteria from pET19-b expression vector (Merck Biosciences GmbH, Schwalbach, Germany). The murine monoclonal anti-p110a and anti-p85 antibodies have been described by Klippel et al. (supra).

Example 2

Preparation of Nucleic Acid Molecules/siRNAs

The molecules and compounds of the present invention can be synthesized by any of the methods which are well-known in the art for synthesis of ribonucleic (or deoxyribonucleic) oligonucleotides. For example, a commercially available machine (available, inter alia, from Applied Biosystems) can be used; the oligonucleotides are prepared for example according to the sequences disclosed herein and also according to known genes.

The strands are synthesized separately and then are annealed to each other in the tube.

The molecules of the invention may be synthesized by procedures known in the art e.g. the procedures as described in Usman et al., 1987, *J. Am. Chem. Soc.*, 109, 7845; Scaringe et al., 1990, *Nucleic Acids Res.*, 18, 5433; Wincott et al., 1995, *Nucleic Acids Res.* 23, 2677-2684; and Wincott et al., 1997, *Methods Mol. Bio.*, 74, 59, and may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The linker can be a polynucleotide linker or a non-nucleotide linker.

For further information, see for example PCT publication No. WO 2004/015107 (atugen AG).

In the context of the RNAster molecule disclosed herein, having one of the following structures:

```
5' oligo1 (sense)       LINKERA  Oligo2 (sense)      3'   (Strand 1)

3' oligo1 (antisense)   LINKERB  Oligo3 (sense)      5'   (Strand 2)

3' oligo3 (antisense)   LINKERC  oligo2 (antisense)  5'   (Strand 3)
or

5' oligo1 (sense)       LINKERA  Oligo2 (antisense)  3'   (Strand 1)

3' oligo1 (antisense)   LINKERB  Oligo3 (sense)      5'   (Strand 2)

3' oligo3 (antisense)   LINKERC  oligo2 (sense)      5'   (Strand 3)
or

5' oligo1 (sense)       LINKERA  oligo3 (antisense)  3'   (Strand 1)

3' oligo1 (antisense)   LINKERB  oligo2 (sense)      5'   (Strand 2)

5' oligo3 (sense)       LINKERC  oligo2 (antisense)  3'   (Strand 3)
``` each of strand 1, strand 2 and strand 3 is synthesized separately and the three strands are then mixed together to form the RNAstar molecule. Therefore, although the three structures represented above give rise to a similar RNAstar molecule, they are not identical. Note that the numbering of the strands as above is for the purpose of simplification only and is not intended to be limiting in any way.

Example 3

Structures of the Molecules of the Present Invention

As will be described below, the structures of the molecules of the present invention are exemplified using two model siRNA sequences, one which targets the TGaseII gene (see co-assigned patent application publication no. WO 2005/072057) and another which targets the HNOEL gene (see co-assigned patent application publication no. WO 2004/112565). However, this is not intended to be limiting in any way, and the siRNA sequences can be replaced with an appropriate sequence which will target any gene, siRNA inhibition of which is desirable. The sequences used herein are intended as teaching examples which demonstrate the molecular structure only.

1) Structure 1: Interrupted Antisense Strand with a Minimal Linker

```
Variant Ia
Seq02-s            5'       aagagcgagaugaucuggaadTsdTuuagagaagaucuacguguuagdTsdT 3'    (SEQ ID NO: 9)

Seq04a-as          3' dTsdTuucucgcucuacuagaccuu   dTsdTucucuucuagaugcacaauc 5'        (SEQ ID NO: 10)

Variant Ib
Seq02b-s           5'        agagcgagaugaucuggaadTsdTuuagagaagaucuacguguuadTsdT 3'     (SEQ ID NO: 11)

TGas + HNas        3' dTsdTucucgcucuacuagaccuu   dTsdTucucuucuagaugcacaau 5'          (SEQ ID NO: 12)

Variant Ic
Seq02 c-s          5'       aagagcgagaugaucuggaadTsdTuuagagaagaucuacguguuagdTsdT 3'   (SEQ ID NO: 13)

Seq04 c-as         3' dTsdTuucucgcucuacuagaccuu   dTsdTucucuucuagaugcacaauc 5'        (SEQ ID NO: 14)

Variant Ib/2
Seq02b/2-s         5' agagcgagaugaucuggaarUsrUagagaagaucuacguguua 3'                  (SEQ ID NO: 15)

TGas/2 + HNas/2    3' ucucgc ucuacuagaccuu       ucucuucuagaugcacaau 5'               (SEQ ID NO: 16)
```

2) Structure 2: Complete Base-Pairing with a Minimal Linker

```
Variant Id
Seq01-s    5'      agagcgagaugaucuggaadTsdTaaagagaagaucuacguguuadTsdT 3'   (SEQ ID NO: 17)

Seq01-as   3' dTsdTucucgcucuacuagaccuuaadTsdTucucuucuagaugcacaau 5'        (SEQ ID NO: 18)
```

3) Structure 3: Minimal Loop Linker

```
Variant Ie
Seq03-s    5'      agagcgagaugaucuggaadTsdTagagaagaucuacguguuadTsdT 3'   (SEQ ID NO: 19)

Seq03-as   3' dTsdTucucgcucuacuagaccuudTsdTucucuucuagaugcacaau 5'        (SEQ ID NO: 20)

Variant If
Seq02-s    5'      aagagcgagaugaucuggaadTsdTuuagagaagaucuacguguuagdTsdT (SEQ ID NO: 21)
           3'

Seq02-as   3' dTsdTuucucgcucuacuagaccuuuudTsdTucucuucuagaugcacaauc 5'    (SEQ ID NO: 22)
```

4) Structure 4: Triple Stranded "Star"-Like Structure

```
HEG-Linker: Hexaethylenglycol
SeqX1 5'      agagcgagaugaucuggaadTsdTaaHEGuuaaagagaagaucuacguguuadTsdT 3'   (SEQ ID NO: 23)

SeqX2 3' dTsdTucucgcucuacuagaccuuaauuHEGaadTsdTuuuaguagguaacaaccc 5'         (SEQ ID NO: 24)

SeqX3 3' dTsdTggguucguuaccuacuaaaaauuHEGaadTsdTucucuucuagaugcacaau 5'        (SEQ ID NO: 25)

TTTT-Linker: poly (5'-2'deoxythymidyl-3'-phosphate)

Variant Ig
SeqX1 5'      agagcgagaugaucuggaadTsdTaaTTTTuuaaagagaagaucuacguguuadTsdT 3'  (SEQ ID NO: 26)

SeqX2 3' dTsdTucucgcucuacuagaccuuaauuTTTTaadTsdTuuuaguagguaacgaaccc 5'       (SEQ ID NO: 27)

SeqX3 3' dTsdTggguucguuaccuacuaaaaauuTTTTaadTsdTucucuucuagaugcacaau 5'       (SEQ ID NO: 28)
```

Note that it may be easier to synthesize the TTTT linker molecule than the HEG-linker molecule.

5) Structure 5: Combination of dsRNA(1) and dsRNA(2) by RNA-Linker

Example: Variant IIa/2

```
Seq02b/3-s      5' agagcgagaugaucuggaaAAAAAAAAAagagaagaucuacguguua 3'    (SEQ ID NO: 29)

TGas/2 + HNas/2 3' ucucgcucuacuagaccuu       ucucuucuagaugcacaau 5'      (SEQ ID NO: 30)
```

Note that the above structure may be cleaved endogenously by RNase.

6) Structure 6: Combination of dsRNA(1) and dsRNA(2) by DNA-Linker
Example

```
                5' agagcgagaugaucuggaaTTTTTTTTTagagaagaucuacguguua 3'    (SEQ ID NO: 31)

TGas/2 + HNas/2 3' ucucgcucuacuagaccuu       ucucuucuagaugcacaau 5'      (SEQ ID NO: 32)
```

Note that the above structure may be cleaved endogenously by DNase.

7) Structure 7: Combination of dsRNA(1) and dsRNA(2) by a Disulfide Linker
Example: Variant IIIa/1

```
Seq02b/5-s      5' agagcgagaugaucuggaa--SS--agagaagaucuacguguua 3'       (SEQ ID NO: 33)

TGas/2 + HNas/2 3' ucucgcucuacuagaccuu       ucucuucuagaugcacaau 5'      (SEQ ID NO: 34)
```

Note that the above structure may be cleaved endogenously under a reducing environment or by disulfide reductases. Additional references for the preparation of molecules possessing this structure include: BA Connolly and P Rider "Chemical synthesis of oligonucleotides containing a free sulphydryl group and subsequent attachment of thiol specific probes" Nucleic Acids Res., June 1985; 13: 4485-4502.; N D Sinha and R M Cook "The preparation and application of functionalised synthetic oligonucleotides: III. Use of H-phosphonate derivatives of protected amino-hexanol and mercapto-propanol or -hexanol" Nucleic Acids Res., March 1988; 16: 2659-2669.; R K Gaur, P Sharma, and K C Gupta "A simple method for the introduction of thiol group at 5'-termini of oligodeoxynucleotides" Nucleic Acids Res., June 1989; 17: 4404.; A Kumar, S Advani, H Dawar, and G P Talwar "A simple method for introducing a thiol group at the 5'-end of synthetic oligonucleotides" Nucleic Acids Res., August 1991; 19: 4561.

8) Structure 8: Combination of dsRNA(1) and dsRNA(2) by a Peptide Linker
Example: Variant Ib/2

```
Seq02b/2-s      5' agagcgagaugaucuggaaX-Gly-Phe-Gly-Yagagaagaucuacguguua 3'
[SEQ ID NOs: 35 and 56 (nucleotides); SEQ ID NO: 36 (peptides)]
TGas/2+HNas/2   3' _ucucgcucuacuagaccuu       _ucucuucuagaugcacaau 5'
[SEQ ID NO: 37]
```

Note that the above structure may be cleaved endogenously by several specific or non-specific peptidases. Additional references for the preparation of molecules possessing this structure include: M Antopolsky and A Azhayev "Stepwise Solid-Phase Synthesis of Peptide-Oligonucleotide Conjugates on New Solid Supports" in Perspectives in Nucleoside and Nucleic Acid Chemistry, p. 275-285, Edited by V. Kisakürek and H. Rosemeyer, Wiley, Verlag Helvetica Chimica Acta 2000.; D A Stetsenko and M J Gait "Chemical Methods for Peptide-Oligonucleotide Conjugate Synthesis" in Oligonucleotide Synthesis Methods and Applications, Edited by Piet Herdewijn, Methods in Molecular Biology Volume 288, Humana Press 2005.

All the above structures can be constructed with or without 5'-6FAM (6-Carboxy-Fluoresceine) on the sense strand-sense; additionally, alternative modifications for the RNA nucleotides include 2'-O-Methyl, 2'-Fluoro, 2'-OAllyl and also some base modifications (Beaucage, S. L.; Iyer, R. P.; Tetrahedron, 1992, 48, 2223-2311 and Beaucage, S. L.; Iyer, R. P.; Tetrahedron, 1993, 49, 6123-6194). Alternative modifications for the DNA nucleotides include base modified DNA; see also Beaucage, S. L.; Iyer, R. P.; Tetrahedron, 1992, 48, 2223-2311 and Beaucage, S. L.; Iyer, R. P.; Tetrahedron, 1993, 49, 6123-6194.

Note that in the above structures, dT or T indicate desoxyribothymidine (DNA); s indicates phosphorothioate ($PO_3S$ instead of $PO_4$); U, A, G, and C indicate 2'-O-Methyl-Ribouridine (RNA), 2'-O-Methyl-Riboadenosine (RNA), 2'-O-Methyl-Riboguanosine (RNA) and 2'-O-Methyl-Ribocytidine (RNA) respectively; U, A, G and C indicate ribouridine (RNA), riboadenosine (RNA), riboguanosine (RNA) and ribocytidine (RNA) respectively; HEG indicates hexaethylenglycol and 6FAM indicates 6-Carboxy-Fluoresceine.

Example 4

Experimental Results

Controls used for the testing of the molecules of the present invention were two siRNAs against two separate genes, TGaseII and HNOEL, each which the assignee of the present invention has already showed to inhibit effectively the corresponding gene (see PCT publications WO 2005/072057 and WO 2004/112565 respectively). The two molecules were combined in the test tube and compared to the efficacy of molecules possessing the above described structures, wherein both these siRNAs are encoded in the one molecule. p53 siRNA was also used as a control.

```
TGaseII
TGaseII-s    5'       agagagagaugaucuggaadTsdT 3'    (SEQ ID NO: 38)
TGaseII-as   3'  dTsdTucucgcucuacuagaccuu  5'        (SEQ ID NO: 39)

HNOEL
HNOEL-s      5'       agagaagaucuacguguuadTsdT 3'    (SEQ ID NO: 40)
HNOEL-as     3'  dTsdTucucuucuagaugcacaau  5'        (SEQ ID NO: 41)

p53
p53-s        5'       cccaagcaauggaugauuudTsdT 3'    (SEQ ID NO: 42)
p53-as       3'  dTsdTgggguucguuaccuacuaaa 5'        (SEQ ID NO: 43)
```

Additional molecules used as controls were the above molecules with and without sense 5'FAM, designated TGaseII-s and HNOEL-s.

siRNA Transfection with Monomers Tandem and RNAstar siRNA Molecules $2 \times 10^5$ tested cells were seeded per well in 6-well plates (70-80% confluent). After 24 hours, cells were transfected with siRNA oligos using Lipofectamine 2000 reagent (Invitrogen) at a final concentration of 500 μM, 5 nM and 20 nM. PTEN-Cy3 oligos or FAM labeled oligos were used as a positive control for transfection; PTEN-Cy3, MR3 and GFPsi molecules were used as negative control for siRNA activity. 48 h-72 h after transfection cells were harvested and RNA or proteins were extracted from cells. Transfection efficiency was tested by fluorescent microscopy or by FACS (using FL-2 filter (for Cy3) or FL-1 filter (for FAM)).

siRNA Sample Preparation:

For Each Transfected Well:

Dilute 3 ul lipofectamine 2000 reagent in 250 ul serum free medium, and incubate for 5 min at RT.

Dilute siRNA molecules as mention below:

Oligos:

PTEN Cy3 stock $1.5 \times 10^6$ nM (dilute 1:150 to final concentration of 10 uM in PBS)

Monomers/tandem/RNAstar stock 100 uM (dilute 1:10 to final concentration of 10 uM in PBS)

TABLE 1

| Oligos | No of wells | Final volume | SiRNA stock 10 uM |
|---|---|---|---|
| 20 nM (1:500) | 3 | 6 ml | 750 ul medium + 12 ul SiRNA |
| 5 nM (1:4 of 20 nM) | | | 250 ul from 20 nM + 750 ul Medium (drop 450 ul before adding lipofectamine) |
| 500 pM (1:10 of 5 nM) | | | 50 ul from 5 nM + 450 ul medium |

Combine Lipofectamine 2000 Reagent with siRNA (1:1 volume), mix gently and incubate at RT for 20 min Transfection Replace medium with 1.5 ml fresh growth medium (containing serum).

Add Lipofectamine/siRNA complex onto cells (500 ul per well), and rock the plate back and forth (2 ml final volume in each well)

Incubate cells at 37° C. in a CO2 incubator.

Cells Used for siRNA Activity Examination

TABLE 2

| Cell line | Tested gene | Species tested gene | Expression type |
|---|---|---|---|
| HFL-1 | TGaseII, p53, HNOEL | Human | Endogenous |
| 293 | TGASEII | Rat | Exogenous |
| 293 | HNOEL | Human | Exogenous |
| NRK49 | TGASEII | Rat | Exogenous |
| HCT116 | P53 | Human | Endogenous/5Fu | p53 was induced in HCT116 cells following treatment with 25 ug/ml 5Fu (5Fu was added in the last 8 h of experiment, before harvesting cells).

Results:

HNOEL Monomer Molecule Activity:

Western blot analysis of HNOEL expression in 293 cells expressing exogenous human HNOEL cDNA, following HNOEL+2 nt (additional overhangs) and blunt siRNA transfection is presented in FIG. 1a.

TGASEII Monomer Activity:

qPCR analysis of TGASEII expression in 293 cells expressing exogenous rat TGASEII cDNA, following TGASE+2 nt and blunt siRNA transfection is presented in Table 3 as % of the control expression

TABLE 3

| | SiRNA conc. | | |
|---|---|---|---|
| | 20 nM | 5 nM | 0.5 nM |
| 293 cellls | 100% | | |
| PTEN-Cy3 | 143% | | |
| MR3 | 174% | | |
| TGASEII | 22% | 7.8% | 67% |
| TGASEII + 2 nt | 34% | 27% | 45% | p53 Monomer Activity:

qPCR analysis of p53 expression in HFL-1 cells expressing endogenous p53, following p53+2 nt siRNA transfection is presented in FIG. 1b as % of the control p53 expression in HFL-1 cells.

A western blot analysis of p53 expression in 5Fu treated p53-wt HCT116 cells, following p53+2 nt siRNA transfection is presented in FIG. 1c.

Transfection Efficiency of Monomer, Tandem and RNAstar Molecules (FACS Using FAM-Labeled Molecules).

The results in Tables 4-5 below represent the comparison of transfection efficiency of the tested molecules in 293 cells.

TABLE 4

Experiment 1

| 20 Nm siRNA | % of transfected cells | FAM intensity | 5 nM siRNA | % of transfected cells | FAM intensity |
|---|---|---|---|---|---|
| TGASEII + 2 nt | 74% | 80 | | 44% | 30 |
| HNOEL + 2 nt | 80% | 59 | | 41% | 29 |
| SeqO2 | 72% | 33 | | 60% | 34 |
| SeqO2b | 72% | 32 | | 70.5% | 44 |
| SeqO2c | 75% | 34 | | 71.5% | 41 |

TABLE 5

Experiment 2

| 20 Nm siRNA | % of transfected cells | FAM intensity | 5 nM siRNA | % of transfected cells | FAM intensity |
|---|---|---|---|---|---|
| P53 + 2 nt | 72% | 90 | | 43% | 35 |
| TGASEII + 2 nt | 64% | 50 | | 26% | 26 |
| HNOEL + 2 nt | 61% | 64 | | 21% | 27 |
| SeqO2b | 80% | 85 | | 60% | 48 |
| RNAstar | 65% | 53 | | 50% | 40 |

Figure 2:
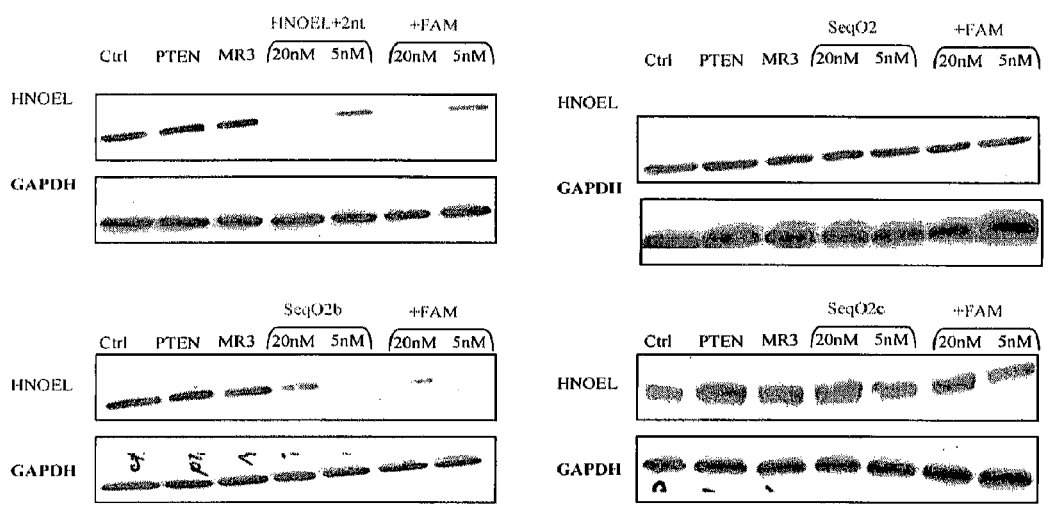

HNOEL Monomer and Tandem Molecules Activity on HNOEL Gene Expression:

The results of a western blot analysis of HNOEL expression in 293 cells expressing exogenous human HNOEL cDNA, following HNOEL+2 nt and tandem siRNA transfection are presented in FIG. 2.

TGASEII Monomer and Tandem Molecules Activity on TGASEII Gene Expression:

The results of a qPCR analysis of TGASEII expression in NRK49 cells expressing exogenous rat TGASEII cDNA, following TGASE+2 nt and tandem siRNA transfection is presented in Table 6 as % of control TGASEII expression in NRK49 cells.

TABLE 6

| | SiRNA concentration | | | |
|---|---|---|---|---|
| | 20 nM | 5 nM | 20 nM | 5 nM |
| NRK49 CELLS | 100% | | | |
| PTEN-Cy3 | 116% | | | |
| MR3 | 60% | | | |
| HNOEL | 95% | 136% | 123% | 40% |
| TGASEII | 46% | 61% | 56% | 91% |
| SeqO2 | 37% | 39% | 37% | 62% |
| SeqO2b | 28% | 36% | 14% | 24% |
| SeqO2c | 36% | 43% | 33% | 58% |

RNAstar Molecule, Activity on p53 TGASEII and HNOEL Genes Expression:

The results of a qPCR analysis of TGASEII, HNOEL and p53 expression in HFL-1 cells expressing endogenous genes, following RNAstar transfection are presented in Tables 7-8 as % of control TGASEII, HNOEL or p53 expression in HFL-1 cells.

TABLE 7

Experiment 1

| | p53 gene | TGaseII gene | HNOEL gene |
|---|---|---|---|
| HFL-1 cells | 100% | 100% | 100% |
| PTEN | 130% | 82% | 110% |
| GFPsi | 111% | 71% | 102% |
| P53 + 2 nt_20 nM | 28% | 104% | 119% |
| 5 nM | 33% | 70% | 100% |
| 0.5 nM | 87% | 71% | 103% |
| HNOEL + 2 nt_20 nM | 105% | 91% | 65% |
| 5 nM | 113% | 98% | 91% |
| 0.5 nM | 131% | 108% | 108% |
| TGASEII + 2 nt_20 nM | 88% | 96% | 84% |
| 5 nM | 156% | 111% | 119% |
| 0.5 nM | 114% | 92% | 105% |
| RNAstar_20 nM | 125% | 104% | 99% |
| 5 nM | 136% | 106% | 115% |
| 0.5 nM | 81% | 108% | 112% |

TABLE 8

Experiment 2

| | P53 gene | TGASEII gene | HNOEL gene |
|---|---|---|---|
| PTEN 20 nM | 100% | 100% | 100% |
| GFPsi_20 nM | 177% | 109% | 124% |
| P53 + 2 nt_20 nM | 54% | 14.9% | 9.7% |
| 5 nM | 25.7% | 9.7% | 7% |
| TGASEII + 2 nt_20 nM | 117% | 35% | 97% |
| 5 nM | 26% | 72% | 57% |
| HNOEL + 2 nt_20 nM | 95% | 77% | 59% |
| 5 nM | 110% | 85% | 66% |
| TGASE/HNOEL + 2 nt_20 nM | 89% | 32% | 32% |
| 5 nM | 49% | 32% | 30% |
| TGASEII/HNOEL/P53 + 2 nt_20 nM | 14% | 27% | 49% |
| 5 nM | 44% | 69% | 80% |
| RNAstar_20 nM | 61% | 34% | 40% |
| 5 nM | 163% | 115% | 96% |

Figure 3:
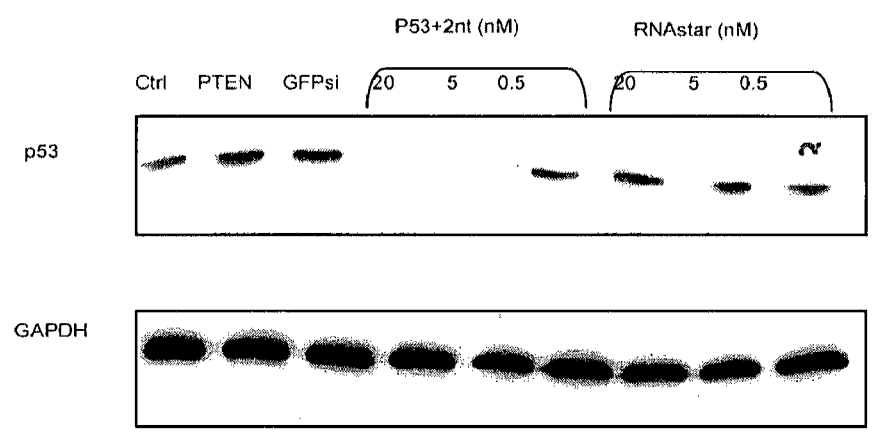

Effect of the RNAstar Molecule on p53 Gene Expression:

The results of a Western blot analysis of p53 expression in 5Fu treated HCT116 cells, following RNAstar transfection are presented in FIG. 3.

The transfection efficiency of RNA star molecule in HFL-1 cells is presented in Table 9.

TABLE 9

| % of transfected cells | 20 nM | 5 nM |
|---|---|---|
| SeqO2b | 36% | 20% |
| RNAstar | 15% | 14% |

Comparison Between the Activity of Co-Transfected HNOEL/TGASEII Monomers and Tandem Molecules:

The results of a qPCR analysis of HNOEL and TGASEII expression in HFL-1 cells following transfection of tandem SeqO2b or SeqO2b/2 siRNA molecules and co transfection of HNOEL and TGASEII monomers (blunt and +2 nt molecules) are presented in Tables 10-11 as % of control expression (TGASEII or HNOEL) in HFL-1 cells.

TABLE 10

Experiment 1

|  | TGaseII gene | HNOEL gene |
|---|---|---|
| HFL-1 cells | 100% | 100% |
| PTEN | 108% | 147% |
| GFPsi | 128% | 122% |
| SeqO2b | 28% | 42% |
| TGaseII | 38% | 137% |
| HNOEL | 90% | 28% |
| TGaseII/HNOEL | 20% | 20% |
| TGaseII + 2 nt | 44% | 98% |
| HNOEL + 2 nt | 86% | 67% |
| TGaseII/HNOEL + 2 nt | 83% | 82% |

(20 nM concentration for all tested oligos)

TABLE 11

Experiment 2

|  | TGaseII gene | HNOEL gene |
|---|---|---|
| PTEN__20 nM | 100% | 100% |
| GFPsi__20 nM | 109% | 124% |
| SeqO2b__20 nM | 32% | 43% |
| 5 nM | 15% | 25% |
| SeqO2b/2__20 nM | 11% | 8% |
| 5 nM | 13% | 16% |
| TGaseII__20 nM | 83% | 42% |
| 5 nM | 66% | 59% |
| HNOEL__20 nM | 16% | 58% |
| 5 nM | 14% | 15% |
| TGaseII/HNOEL__20 nM | 96% | 9% |
| 5 nM | 88% | 7% |
| TGaseII + 2 nt__20 nM | 35% | 97% |
| 5 nM | 72% | 57% |
| HNOEL + 2 nt__20 nM | 77% | 59% |
| 5 nM | 85% | 65% |
| TGaseII/HNOEL + 2 nt__20 nM | 32% | 32% |
| 5 nM | 32% | 30% |

Figure 4:
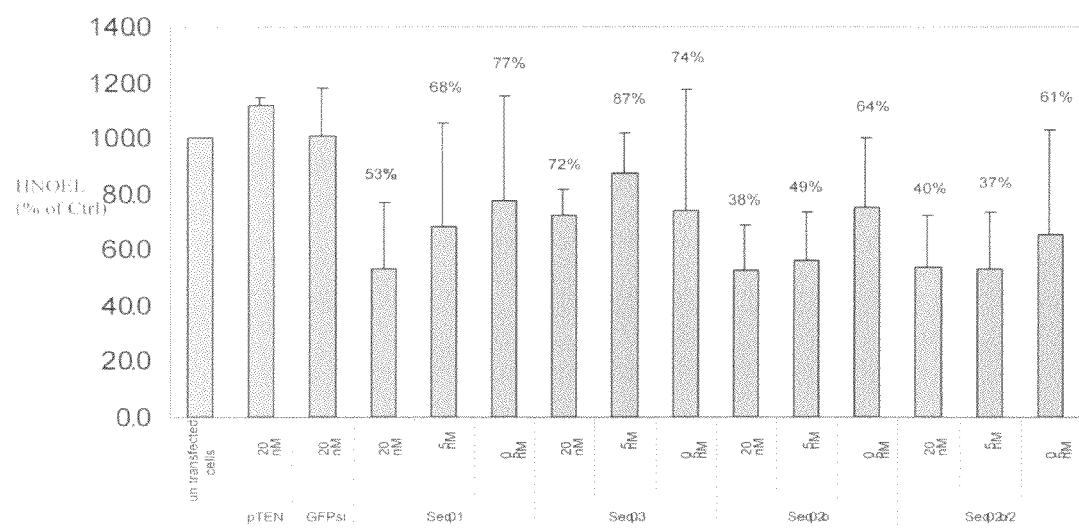
Figure 4B:
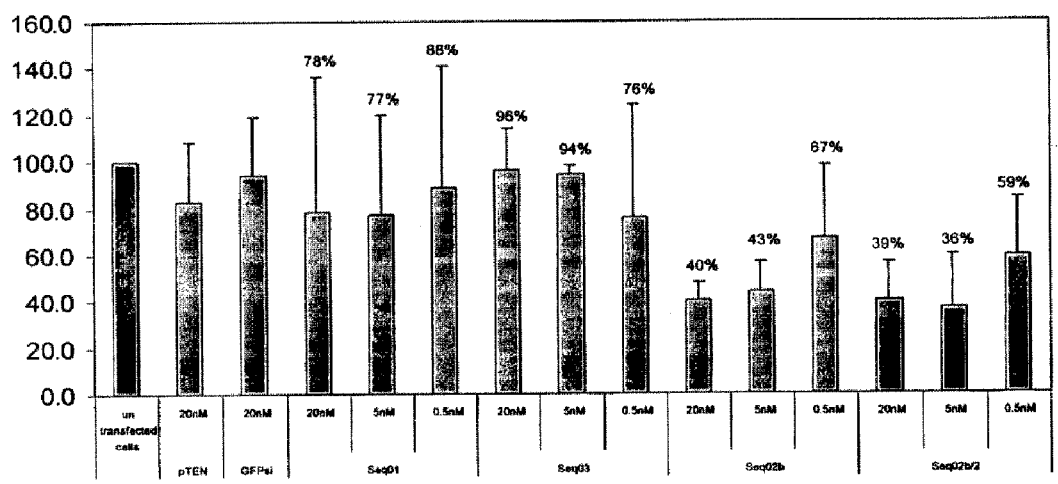

Effect of Tandem Molecules on TGase and HNOEL Expression:

The results of a qPCR analysis of HNOEL and TGASEII expression in HFL-1 cells following transfection with tandem variant molecules (SeqO1, SeqO3, SeqO2b, SeqO2b/2) are presented in FIG. 4 a+b (a=HNOEL, b=TGASEII) as % of control TGASEII or HNOEL expression in HFL-1 cells.

Effect of RNAstar Molecule on p53 TGASEII and HNOEL Gene Expression:

The results of a qPCR analysis of TGASEII, HNOEL and p53 expression in HFL-1 cells expressing endogenous genes, following RNAstar transfection are presented in Tables 12-13 as % of control TGASEII, HNOEL or p53 expression in HFL-1 cells.

TABLE 12

Experiment 1

|  | P53 gene | TGASEII gene | HNOEL gene |
|---|---|---|---|
| HFL-1 cells | 100% | 100% | 100% |
| PTEN | 130% | 82% | 110% |

TABLE 12-continued

Experiment 1

|  | P53 gene | TGASEII gene | HNOEL gene |
|---|---|---|---|
| GFPsi | 111% | 71% | 102% |
| P53 + 2 nt__20 nM | 28% | 104% | 119% |
| 5 nM | 33% | 70% | 100% |
| 0.5 nM | 87% | 71% | 103% |
| HNOEL + 2 nt__20 nM | 105% | 91% | 65% |
| 5 nM | 113% | 98% | 91% |
| 0.5 nM | 131% | 108% | 108% |
| TGASEII + 2 nt__20 nM | 88% | 96% | 84% |
| 5 nM | 156% | 111% | 119% |
| 0.5 nM | 114% | 92% | 105% |
| RNAstar__20 nM | 125% | 104% | 99% |
| 5 nM | 136% | 106% | 115% |
| 0.5 nM | 81% | 108% | 112% |

TABLE 13

Experiment 2

Figure 5:
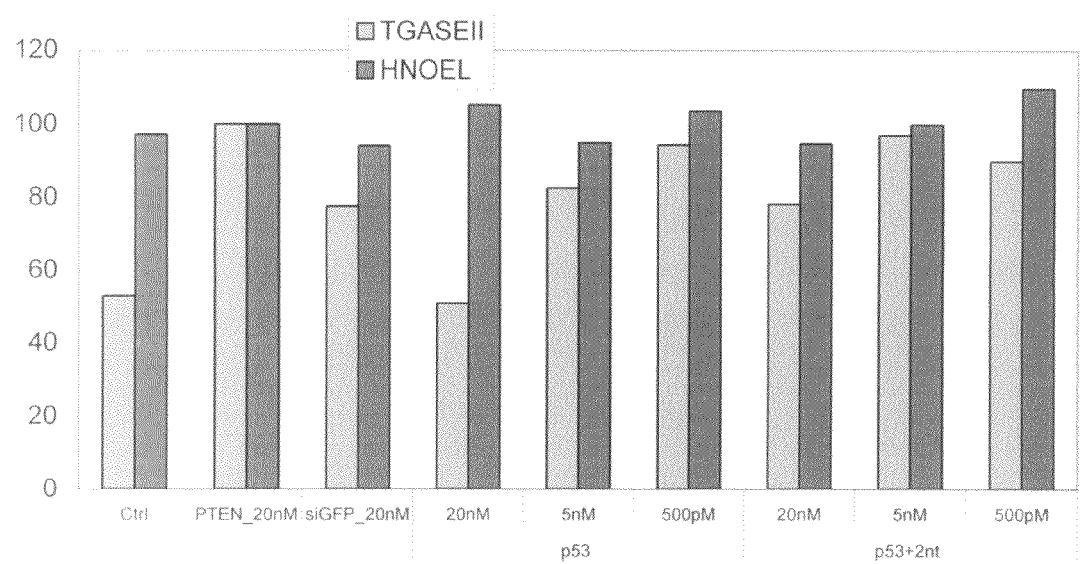

|  | P53 gene | TGASEII gene | HNOEL gene |
|---|---|---|---|
| PTEN 20 nM | 100% | 100% | 100% |
| GFPsi__20 nM | 177% | 109% | 124% |
| P53 + 2 nt__20 nM | 54% | 14.9% | 9.7% |
| 5 nM | 25.7% | 9.7% | 7% |
| TGASEII + 2 nt__20 nM | 117% | 35% | 97% |
| 5 nM | 26% | 72% | 57% |
| HNOEL + 2 nt__20 nM | 95% | 77% | 59% |
| 5 nM | 110% | 85% | 66% |
| TGASE/HNOEL + 2 nt__20 nM | 89% | 32% | 32% |
| 5 nM | 49% | 32% | 30% |
| TGASEII/HNOEL/P53 + 2 nt__20 nM | 14% | 27% | 49% |
| 5 nM | 44% | 69% | 80% |
| RNAstar__20 nM | 61% | 34% | 40% |
| 5 nM | 163% | 115% | 96% | p53 Blunt and p53+2 nt Monomers Activity on TGASEII and HNOEL Expression:

The results of a qPCR analysis of TGASEII, and HNOEL expression in HFL-1 cells expressing endogenous genes, following transfection by a "single" p53 siRNA molecule are presented in FIG. 5 as % of TGASEII and HNOEL expression in HFL-1 cells.

All of the above results demonstrate the efficacy of the tandem molecules of the present invention in inhibiting the endogenous genes which they target.

Example 5

Additional Experimental Results with RNAstar

The activity of the RNAstar gapped molecules was examined 72 h following transfection. The control active siRNAs chosen for the assay were MRH2 (HNOEL), HMRG1 (TGASEII), QH1 (P53) and SeqO2b_SeqO2b/2 (TGASEII and HNOEL) siRNA molecules, which have been found to be active in down-regulating their target genes by the assignee of the present invention. PTEN siRNA and GFP siRNA were used as negative controls.

The following cell lines were used in the study:

| Cell line | Tested genes | Species tested gene | Expression type | Activity observation |
|---|---|---|---|---|
| HFL1 | TGaseII, p53, HNOEL | Human | Endogenous | qPCR |
| 293 | HNOEL | Human | Exogenous | qPCR/Western blot |
| NRK49 | TGase II | Rat | Exogenous | qPCR/Western blot |
| HCT116 | p53 | Human | Endogenous, 5FU induced | Western blot |

The different variants tested and the genes they target are presented in FIG. 6; underlined nucleotides were modified, but it is envisaged that unmodified nucleotides may also be used.

Results

A) qPCR Analysis of HNOEL Expression in HFL-1 Cells Expressing Endogenous Human HNOEL Gene Following Transfection with Gapped RNAstar:

The data in Table 14 demonstrate residual (% of PTEN) human HNOEL expression in HFL-1 cells.

TABLE 14

| | siRNA concentration | | |
|---|---|---|---|
| | 0.5 nM | 5 nM | 20 nM |
| PTEN-Cy3 | | | 100% |
| SiGFP | | | 199% |
| HNOEL monomer | 111% | 144% | 129% |
| SeqO2b/2 (positive Control) | 104% | 37% | 16% |
| Complex-p53/HNOEL/TGASEII siRNA monomers | 115% | 70% | 82% |
| RNAstar | 39% | 33% | 30% |
| Ig/4 (HNOEL) | 89% | 207% | 181% |
| Ig/5 (gapped RNAstar) | 149% | 126% | 63% |
| Ig/6 (gapped RNAstar) | 115% | 37% | 41% |
| Ig/7 (gapped RNAstar) | | | 14% |

B) qPCR Analysis of TGASEII Expression in HFL-1 Cells Expressing Endogenous Human TGASEII Gene Following Transfection with Gapped RNAstar:

The data in Table 15 demonstrate residual (% of PTEN) human TGASEII expression in HFL-1 cells.

TABLE 15

| | siRNA concentration | | |
|---|---|---|---|
| | 0.5 nM | 5 nM | 20 nM |
| PTEN-Cy3 | | | 100% |
| siGFP | | | 131% |
| TGASEII monomer | 144% | 134% | 113% |
| SeqO2b/2 (positive Control) | 137% | 145% | 103% |
| Complex-p53/HNOEL/TGASEII siRNA monomers | 164% | 88% | 93% |
| RNAstar | 63% | 89% | 62% |
| Ig/2 (TGASEII) | 134% | 157% | 113% |
| Ig/5 (gapped RNAstar) | 137% | 83% | 38% |
| Ig/6 (gapped RNAstar) | | 28% | 53% |
| Ig/7 (gapped RNAstar) | | | 50% |

C) qPCR Analysis of p53 Expression in HFL-1 Cells Expressing Endogenous Human p53 Gene Following Transfection with Gapped RNAstar:

The data in Table 16 demonstrate residual (% of PTEN) human p53 expression in HFL-1 cells.

TABLE 16

| | siRNA concentration | | |
|---|---|---|---|
| | 0.5 nM | 5 nM | 20 nM |
| PTEN-Cy3 | | | 100% |
| siGFP | | | 127% |
| Tp53 monomer | 37% | 24% | 15% |
| Complex-p53/HNOEL/TGASEII siRNA monomers | 89% | 66% | 93% |
| RNAstar | | 92% | 92% |
| Ig/3 (p53) | 97% | 121% | 81% |
| Ig/5 (gapped RNAstar) | 82% | 43% | 23% |
| Ig/6 (gapped RNAstar) | 97% | 52% | 76% |
| Ig/7 (gapped RNAstar) | | | 43% |

D) qPCR Analysis of TGASEII Expression in NRK49 Cells Expressing Exogenous Rat TGASEII Gene Following Transfection with Gapped RNAstar:

The data in Table 17 demonstrate residual (% of Control) rat TGASEII expression in NRK49 cells.

TABLE 17

| | siRNA concentration | | | | | |
|---|---|---|---|---|---|---|
| | 5 nM | | | 20 nM | | |
| | Exp 1 | Exp2 | Average | Exp 1 | Exp2 | Average |
| PTEN-Cy3 | | | | 82% | 109% | 95.5 ± 19 |
| SiGFP | | | | 105% | 75% | 90 ± 21 |
| TGASEII monomer | 64% | 75% | 69.5 ± 7.7 | 87% | 84% | 85.5 ± 2 |
| SeqO2b | | 57% | 57 | | 22% | 22 |
| Complex-p53/HNOEL/TGASEII siRNA monomers | 21% | 73% | 47 ± 37 | 22% | 49% | 35.5 ± 19 |
| RNAstar | 52% | 52% | 52 ± 0 | 66% | 60% | 63 ± 4 |
| Ig/2 (TGASEII) | 94% | | 94 | 65% | | 65 |
| Ig/5 (gapped RNAstar) | 53% | 77% | 65 ± 17 | 55% | 64% | 59.5 ± 6 |
| Ig/6 (gapped RNAstar) | 77% | 58% | 67.5 ± 13 | 61% | 89% | 75 ± 20 |
| Ig/7 (gapped RNAstar) | 16% | 33% | 24.5 ± 12 | 17% | 32% | 24.5 ± 10 |

E) qPCR Analysis of HNOEL Expression in NRK49 Cells Expressing Endogenous Rat HNOEL Gene Following Transfection with Gapped RNAstar:

The data in Table 18 demonstrate residual (% of Control) rat HNOEL expression in NRK49 cells.

TABLE 18

| | siRNA concentration | | | | | |
|---|---|---|---|---|---|---|
| | 5 nM | | | 20 nM | | |
| | Exp 1 | Exp2 | Average | Exp 1 | Exp2 | Average |
| PTEN-Cy3 | | | | 57% | 69% | 63 ± 8 |
| siGFP | | | | 119% | 102% | 110 ± 12 |
| HNOEL monomer | 108% | 72% | 90 ± 25 | 114% | 88% | 101 ± 18 |
| SEQO2B | | 85% | 85 | | 91% | 91 |
| Complex-p53/HNOEL/TGASEII siRNA monomers | 69% | 147% | 108 ± 55 | 62% | 132% | 97 ± 49 |
| RNAstar | 74% | 180% | 127 ± 75 | 154% | 156% | 155 ± 1 |
| Ig/5 (gapped RNAstar) | 57% | 200% | 128.5 ± 101 | 32% | 123% | 77.5 ± 64 |
| Ig/6 (gapped RNAstar) | 44% | 140% | 92 ± 69 | 20% | 122% | 71 ± 72 |
| Ig/7 (gapped RNAstar) | 33% | 146% | 89.5 ± 79 | 39% | 173% | 106 ± 94 |

F) qPCR Analysis of HNOEL Expression in 293 Cells Expressing Exogenous Human HNOEL Gene Following Transfection with Gapped RNAstar:

The data in Table 19 demonstrate residual (% of Control) human HNOEL expression in 293 cells.

TABLE 19

| | siRNA concentration | | | | | |
|---|---|---|---|---|---|---|
| | 5 nM | | | 20 nM | | |
| | Exp 1 | Exp2 | Average | Exp 1 | Exp2 | Average |
| PTEN-Cy3 | | | | 101% | 64% | 82.5 ± 26 |
| siGFP | | | | 118% | 86% | 102 ± 22 |
| HNOEL monomer | 122% | 89% | 105.5 ± 23 | 87% | 115% | 101 ± 20 |
| SeqO2b | | 52% | 52 | | 22% | 22 |
| Complex-p53/HNOEL/TGASEII siRNA monomers | 71% | 81% | 76 ± 7 | 53% | 110% | 81.5 ± 40 |
| RNAstar | 86% | 72% | 79 ± 10 | 45% | 87% | 66 ± 29 |
| Ig/5 (gapped RNAstar) | 64% | 47% | 55.5 ± 12 | 49% | 34% | 41.5 ± 10 |
| Ig/6 (gapped RNAstar) | 77% | 50% | 63.5 ± 19 | 70% | 45% | 57.5 ± 17 |
| Ig/7 (gapped RNAstar) | 103% | 63% | 83 ± 28 | 86% | 50% | 68 ± 25 |

Figure 8:
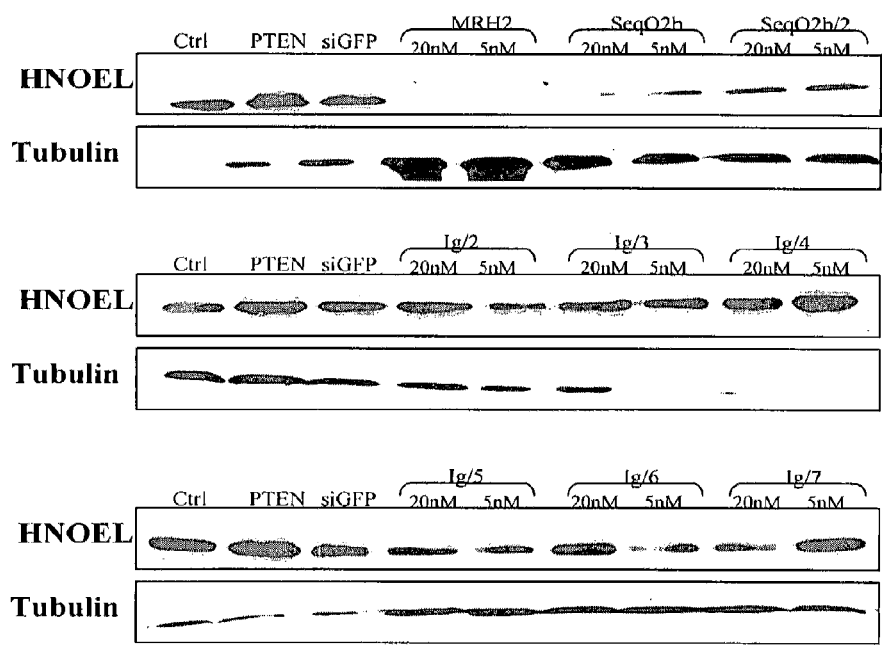
FIG. 8 shows the results of Western blot experiments which demonstrate the activity of molecules of the present invention.

The results of the corresponding Western blots appear in FIG. 8.

Conclusions

The activity of RNAstar molecule on the transcription level of three target genes (p53, HNOEL and TGASEII) was examined. 60% inhibition of HNOEL expression, 4.0-50% inhibition of TGASEII expression, and a little inhibition of p53 expression were observed.

The Ig/5 variant is significantly more active than Ig/6 and Ig/7 variants on p53 gene; the Ig/6 and Ig/7 variants displayed more activity on TGASE and HNOEL genes as compared to the Ig/5 variant; Further, the RNAstar gapped variants appear significantly more active than the non-gapped RNAstar molecule against the three particular targets tested.

In general, the variants tested were active in inhibiting the expression of the target genes; the degree of inhibition varies between each variant/target gene combination. Thus all variants are potentially active against any given gene. Table 20 sums up all experiments conducted.

TABLE 20

| | Exp No | | | | | | | | | | | |
|---|---|---|---|---|---|---|---|---|---|---|---|---|
| | Exp 1 | Exp 2 | Exp 3 | Exp 4 | Exp 5 | Exp 5 | Exp 1 | Exp 2 | Exp 3 | Exp 5 | Exp 1 | Exp 2 |
| | Tested cells | | | | | | | | | | | |
| | HFL-1 qPCR | NRK49 qPCR | 293 qPCR | 293 Western | 293 qPCR | NRK49 qPCR | HFL-1 qPCR | NRK49 qPCR | NRK49 Western | NRK49 qPCR | HFL-1 qPCR | HCT116 Western |
| SeqO2b | | | | +++ | ± | | | | +++ | | | |
| RNAstar | +++ | − | ++ | | + | − | + | ++ | | ++ | − | − |
| Ig/5 | + − | +++ | ++ | + | ++± | − | + | ++ | − | ++ | +++ | +++ |

TABLE 20-continued

| | Exp No | | | | | | | | | | | |
|---|---|---|---|---|---|---|---|---|---|---|---|---|
| | Exp 1 | Exp 2 | Exp 3 | Exp 4 | Exp 5 | Exp 5 | Exp 1 | Exp 2 | Exp 3 | Exp 5 | Exp 1 | Exp 2 |
| | | | | | | Tested cells | | | | | | |
| | HFL-1 qPCR | NRK49 qPCR | 293 qPCR | 293 Western | 293 qPCR | NRK49 qPCR | HFL-1 qPCR | NRK49 qPCR | NRK49 Western | NRK49 qPCR | HFL-1 qPCR | HCT116 Western |
| Ig/6 | +++ | +++ | + | ++ | ++± | − | +++ | + | ++ | ++ | + | +− |
| Ig/7 | +++ | +++ | − | ++ | ++± | − | ++ | +++ | +++ | +++ | ++ | − |

Example 6

Additional Experimental Results with Tandem Structures

Procedure
1. General
 1.1 $2\times10^5$ HFL-1 cells expressing endogenous TGASEII and HNOEL genes were seeded per well in 6-well plate (70-80% confluent).
 1.2 24 h subsequently, cells were transfected with siRNA oligos using the lipofectamine 2000 reagent (Invitrogene) at a final concentration of 10 nM and 20 nM.
  PTEN-Cy3 oligos were used as a positive control for transfection.
  GFPsi molecules were used as a negative control for siRNA activity.
 1.3 72 h after transfection cells were harvested and RNA was extracted from the cells.
 1.4 Transfection efficiency was tested by fluorescent microscopy.
2. Sample Preparation:
For each Transfected Well:
 2.1 Dilute 3 ul lipofectamine 2000 reagent in 250 ul serum free medium, and incubate for 5 min at RT.
 2.2 Dilute siRNA molecules as mentioned below:
 2.3 Oligos:
  PTEN Cy3 stock $1.5\times10^6$ nM (dilute 1:150 to have final concentration of 10 uM with PBS)
  Monomers/tandem stock 100 uM (dilute 1:10 to have final concentration of 10 uM with PBS)

| Oligos | No of wells | Final volume | SiRNA stock 10uM |
|---|---|---|---|
| 20 nM (1:500) | 2 | 4 ml | 500 ul medium + 8 ul siRNA |
| 10 nM (1:1000) | 2 | 4 ml | 500 ul medium + 4 ul siRNA |
| GFPsi 40 nM (1:250) | 2 | 4 ml | 500 ul medium + 16 ul siRNA |

2.4 Combine lipofectamine 2000 Reagent with siRNA (1:1 volume), mix gently and incubate at RT for 20 min
3. Transfection
 3.1 At this time replace cell medium with 1.5 ml fresh growth medium (containing serum).
 3.2 Add lipofectamine/siRNA complex onto cells (500 ul per well), and rock the plate back and forth (2 ml final volume in each well)
 Incubate cells at 37° C. in a CO2 incubator. (medium can be replaced 6 or 24 h after transfection).
Structure of siRNA Variants Used
Variant Ib/2 (SeqO2b/2)

```
                                            (SEQ ID NO: 44)
Seq02b/2-s 5'  agagcgagaugaucuggaarUsrUagagaag
               aucuacguguua 3'

(SEQ ID NO: 45)
TGas/2+HNas/2 3' ucucgcucuacuagaccuu     ucucuuc
                 uagaugcacaau 5'
```

Variant IIa/1 (RNaseH)

```
Seq02b/3-s  5' agagcgagaugaucuggaaAAAAAAAAAagagaagaucuacguguua 3' (SEQ ID NO: 46)

Seq02b/3-as 3' ucucgcucuacuagaccuuuuuuuuuuuucucuucuagaugcacaau 5' (SEQ ID NO: 47)
```

Variant IIa/2 (RNaseH-Control)

```
Seq02b/3-s    5' agagcgagaugaucuggaaAAAAAAAAAagagaagaucuacguguua 3' (SEQ ID NO: 48)

TGas/2+HNas/2 3' ucucgcucuacuagaccuu         ucucuucuagaugcacaau 5' (SEQ ID NO: 49)
```

Variant IIIa/1 (RNase)

```
Seq02b/4-s    5' agagcgagaugaucuggaaCUCUCUCUCagagaagaucuacguguua 3' (SEQ ID NO: 50)

TGas/2+HNas/2 3' ucucgcucuacuagaccuu         ucucuucuagaugcacaau 5' (SEQ ID NO: 51)
```

Variant IIIa/1 (Reductase)

```
Seq02b/5-s     5' agagcgagaugaucuggaa--SS--agagaagaucuacguguua 3'    (SEQ ID NO: 52)

TGas/2+HNas/2 3' ucucgcucuacuagaccuu      ucucuucuagaugcacaau 5'    (SEQ ID NO: 53)
```

Variant Ib/3

```
Seq02b/2-s     5' agagcgagaugaucuggaa       agagaagaucuacguguua 3'    (SEQ ID NO: 54)

TGas/2+HNas/2 3' ucucgcucuacuagaccuurUsrUucucuucuagaugcacaau 5'    (SEQ ID NO: 55)
```

Note that in the above structures linkers are presented in bold, while modified nucleotides are underlined.

Results

Figure 9:
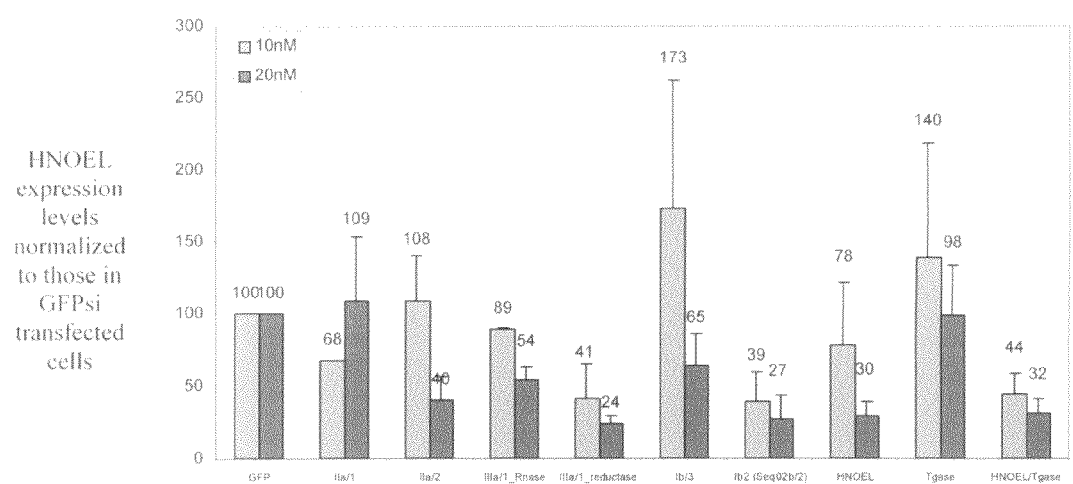
FIGS. 9-10 show further experimental results which demonstrate the efficacy of the molecules of the present invention in down-regulation of various genes—see also Example 6.
Figure 10:
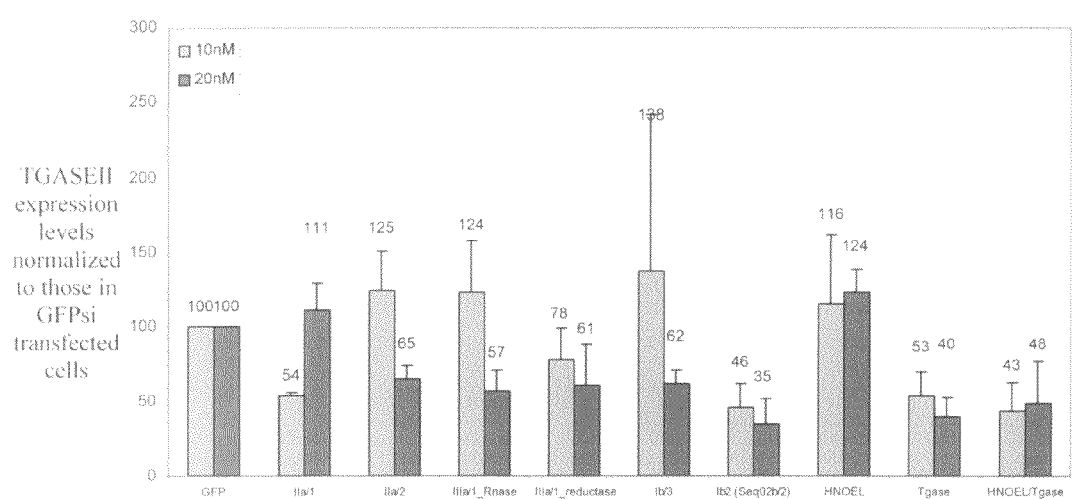

The results are presented in FIGS. 9 and 10 as residual HNOEL or TGASEII expression in HFL-1 cells. Results are an average of 3 independent experiments.

As shown in the Figures:

All tested molecules showed activity. Of the four tested tandem molecules (IIa/1_RNaseH, IIIa/1_RNase, IIIa/1_Reductase and IIa/1_sense gap), variant IIIa/1 reductase showed the highest activity against the target genes examined—approximately, 60% and 80% inhibition in HNOEL expression following transfection of 10 nM and 20 nM, respectively, and 40% inhibition in TGASEII expression following transfection of 20 nM.

Thus, as indicated above for the RNAstar structure, the degree of inhibition varies between each variant/target gene combination. Thus all variants are potentially active against any given gene.

Example 7

Pharmacology and Drug Delivery

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell.

The compounds or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The treatment generally has a length proportional to the length of the disease process and drug effectiveness and the patient species being treated. It is noted that humans are treated generally longer than the mice or other experimental animals exemplified herein.

The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and an oil, especially a vegetable oil and a lipid and suitable mixtures thereof.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin.

According to the present invention, however, any vehicle, diluent, or additive used has to be compatible with the compounds.

Sterile injectable solutions can be prepared by incorporating the compounds utilized in practicing the present invention in the required amount of the appropriate solvent with several of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compound in tablets, suspensions, solutions, emulsions, capsules, powders, syrups and the like are usable. Known techniques which deliver it orally or intravenously and retain the biological activity are preferred. In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-2 weeks or longer, preferably for 24- to 48 hrs or by continuous infusion during a period of 1-2 weeks or longer.

Administration of Compounds of the Present Invention to the Eye

The compounds of the present invention can be administered to the eye topically or in the form of an injection, such as an intravitreal injection, a sub-retinal injection or a bilateral injection.

Further information on administration of the compounds of the present invention can be found in Tolentino et al., *Retina* 24 (2004) 132-138; Reich et al., *Molecular vision* 9 (2003) 210-216.

Pulmonary Administration of Compounds of the Present Invention

The therapeutic compositions of the present invention are preferably administered into the lung by inhalation of an aerosol containing such composition/compound, or by intranasal or intratracheal instillation of said compositions. Formulating the compositions in liposomes may benefit absorption. Additionally, the compositions may include a PFC liquid such as perflubron, and the compositions may be formulated as a complex of the compounds of the invention with polyethylemeimine (PEI).

For further information on pulmonary delivery of pharmaceutical compositions see Weiss et al., *Human gene therapy* 10:2287-2293 (1999); Densmore et al., *Molecular therapy* 1:180-188 (1999); Gautain et al., *Molecular therapy* 3:551-556 (2001); and Shahiwala & Misra, *AAPS PharmSciTech* 5 (2004). Additionally, respiratory formulations for siRNA are described in U.S. patent application No. 2004/0063654 of Davis et el.

Administration of Compounds of the Present Invention to the Ear

A preferred administration mode is directly to the affected portion of the ear or vestibule, topically as by implant for example, and, preferably to the affected hair cells or their supporting cells, so as to direct the active molecules to the source and minimize its side effects. A preferred administration mode is a topical delivery of the inhibitor(s) onto the round window membrane of the cochlea. Such a method of administration of other compounds is disclosed for example in Tanaka et al. (Hear Res. 2003 March; 177(1-2):21-31). Additional modes of administration to the ear are by administration of liquid drops to the ear canal, delivery to the scala tympani chamber of the inner ear by transtympanic injection, or provision as a diffusible member of a cochlear hearing implant.

In the treatment of pressure sores or other wounds, the administration of the pharmaceutical composition is preferably by topical application to the damaged area, but the compositions may also be administered systemically.

Additional formulations for improved delivery of the compounds of the present invention can include non-formulated compounds, compounds covalently bound to cholesterol, and compounds bound to targeting antibodies (Song et al., Antibody mediated in vivo delivery of small interfering RNAs via cell-surface receptors, Nat Biotechnol. 2005 June; 23(6):709-17).

The invention claimed is:

1. A compound consisting of four ribonucleotide strands forming three double-stranded siRNA duplexes and having the structure:

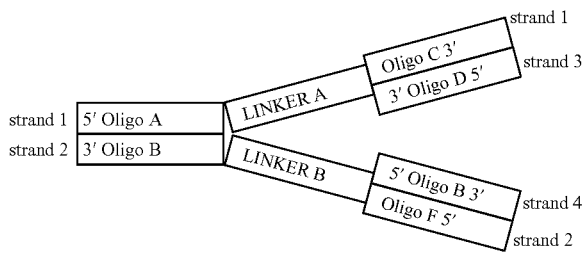

wherein each of oligo A, oligo B, oligo C, oligo D, oligo E and oligo F represents from 19 to 40 consecutive ribonucleotides, each of which ribonucleotides may be modified or unmodified;

wherein strand 1 comprises oligo A which is either a sense portion or an antisense portion of a first siRNA duplex within the compound, strand 2 comprises oligo B which is complementary to at least 19 nucleotides in oligo A, and oligo A and oligo B together form such first siRNA duplex that targets a first target mRNA;

wherein strand 1 further comprises oligo C which is either a sense portion or an antisense portion of a second siRNA duplex within the compound, strand 3 comprises oligo D which is complementary to at least 19 nucleotides in oligo C and oligo C and oligo D together form such second siRNA duplex that targets a second target mRNA;

wherein strand 4 comprises oligo E which is either a sense portion or an antisense portion of a third siRNA duplex within the compound, strand 2 further comprises oligo F which is complementary to at least 19 nucleotides in oligo E and oligo E and oligo F together form such third siRNA duplex that targets a third target mRNA; and wherein linker A is a moiety that covalently links oligo A and oligo C; linker B is a moiety that covalently links oligo B and oligo F, and linker A and linker B can be the same or different.

2. A composition comprising the compound of claim 1 and a pharmaceutically acceptable carrier.

3. The compound of claim 1, wherein each of linker A and linker B is independently a nucleotide linker or a non-nucleotide linker.

4. The compound of claim 3, wherein at least one of linker A or linker B is a non-nucleotide linker.

5. The compound of claim 3, wherein at least one of linker A or linker B is a nucleotide linker.

6. The compound of claim 1, wherein oligo A is a sense portion, oligo C is a sense portion, and oligo E is an antisense portion of the first, the second, and the third siRNA duplex, respectively.

7. The compound according to claim 1, wherein oligo A is a sense portion, oligo C is an antisense portion, and oligo E is an antisense portion of the first, the second, and the third siRNA component, respectively.

8. The compound according to claim 1, wherein oligo A is a sense portion, oligo C is a sense portion, oligo E is a sense portion of the first, the second, and the third siRNA duplex, respectively, and wherein linker A is not the same as linker B.

9. The compound of claim 5, wherein each of linker A and linker B is a nucleotide linker.

10. The compound of claim 5, wherein the nucleotide linker is 2-10 nucleotides in length.

11. The compound of claim 5, wherein at least one of linker A and linker B is a nucleotide linker which comprises the sequence 5' tttt 3'.

12. The compound of claim 5, wherein at least one of linker A and linker B is a DNA linker.

13. The compound of claim 4, wherein at least one of linker A and linker B comprises a disulfide bond.

14. The compound of claim 4, wherein at least one of linker A and linker B comprises a peptide bond.

15. The compound of claim 1, wherein the first target mRNA is identical to either the second target mRNA or the third target mRNA or to both the second target mRNA and the third target mRNA.

16. The compound of claim 1, wherein at least one ribonucleotide in one of oligo A, B, C, D, E or F comprises a modification at the 2' position of the sugar of such ribonucleotide.

17. The compound of claim 16, wherein the modification is a 2'-methyl substitution or a 2'fluoro substitution.

18. The compound of claim 16, wherein the compound comprises 2' sugar modifications on every other ribonucleotide within at least one of oligo A, B, C, D, E, or F.

19. The compound of claim 1, wherein one or more of the first, the second or the third siRNA duplex comprises the structure:

$$5'(N)_x\text{—}Z3' \text{ (antisense portion)}$$

$$3'Z'\text{—}(N')_y5' \text{ (sense portion)}$$

wherein each N and N' is a ribonucleotide which may be modified or unmodified in its sugar, its base or both its sugar and its base;

wherein in each of $(N)_x$ and $(N')_y$ each consecutive N or N' is joined to the next N or N' by a covalent bond; wherein each of x and y is an integer from 19 to 40; and wherein each of Z and Z' may be present or absent, but if present is dTdT, rUrU, dUdU or rTrT and is covalently attached at the 3' terminus of the portion in which it is present.

20. The compound of claim 19, wherein in at least one duplex the covalent bond is a phosphodiester bond;

wherein x=y or x=y−1;

wherein both Z and Z' are absent;

wherein at least one ribonucleotide comprises a 2'-O-Methyl sugar modification and wherein every other ribonucleotide is modified in both the antisense portion and the sense portion, with the ribonucleotides at the 5' terminus and the 3' terminus of the antisense portion being modified in their sugar residues, and the ribonucleotides at the 5' terminus and the 3' terminus of the sense portion being unmodified in their sugar residues.

21. The compound of claim 19, wherein in one or more of the first, the second or the third siRNA duplex Z and Z' are present.

22. The compound of claim 3, wherein at least one of linker A or linker B comprises the sequence 5'dTsdT [5'-2'deoxythymidyl-3'-thiophosphate-5'-2'deoxythymidyl-3'-phosphate].

23. The compound of claim 3, wherein at least one of linker A or linker B comprises the sequence 5'dTsdTuu [5'-2'deoxythymidyl-3'-thiophosphate-5'-2'deoxythymidyl-3'-phosphate-5'-uridyl-3'-phosphate-5'-uridyl-3'-phosphate].

24. The compound of claim 3, wherein at least one of linker A or linker B comprises the sequence 5'dTsdTaa [5'-2'deoxythymidyl-3'-thiophosphate-5'-2'deoxythymidyl-3'-phosphate-5'-adenyl-3'-phosphate-5'-adenyl-3'-phosphate].

25. The compound of claim 3, wherein at least one of linker A or linker B comprises the sequence 5'rUsrU [5'-uridyl-3'-thiophosphate-5'-uridyl-3'-phosphate].

* * * * *

SEQUENCE LISTING

<160> NUMBER OF SEQ ID NOS: 56

<210> SEQ ID NO 1
<211> LENGTH: 50
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(50)
<223> OTHER INFORMATION: n is A, C, U, or G - where up to 48 n residues
      are absent

<400> SEQUENCE: 1
nnnnnnnnnn nnnnnnnnnn nnnnnnnnnn nnnnnnnnnn nnnnnnnnnn        50

<210> SEQ ID NO 2
<211> LENGTH: 50
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(50)
<223> OTHER INFORMATION: n is A, C, G or T - where up to 48 n residues
      are absent

<400> SEQUENCE: 2
nnnnnnnnnn nnnnnnnnnn nnnnnnnnnn nnnnnnnnnn nnnnnnnnnn        50

<210> SEQ ID NO 3
<211> LENGTH: 10
<212> TYPE: PRT
<213> ORGANISM: Artificial sequence
<220> FEATURE:
<223> OTHER INFORMATION: Chemically synthesized sequence
<220> FEATURE:
<221> NAME/KEY: MISC_FEATURE
<222> LOCATION: (1)..(10)
<223> OTHER INFORMATION: Xaa is any amino acid - where up to 9 Xaa
      residues are absent

<400> SEQUENCE: 3

Xaa Xaa Xaa Xaa Xaa Xaa Xaa Xaa Xaa Xaa
1               5                   10

<210> SEQ ID NO 4
<211> LENGTH: 50
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(50)
<223> OTHER INFORMATION: n is A, C, G, U or T - where up to 49 n
      residues are absent

<400> SEQUENCE: 4
nnnnnnnnnn nnnnnnnnnn nnnnnnnnnn nnnnnnnnnn nnnnnnnnnn        50

<210> SEQ ID NO 5
<211> LENGTH: 42
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(40)
<223> OTHER INFORMATION: RNA sequence, wherein n is any ribonucleotide -
      where up to 21 n residues are absent
<220> FEATURE:
<221> NAME/KEY: misc_feature
<222> LOCATION: (41)..(42)
<223> OTHER INFORMATION: nn is absent or present; if present, nn is
      dTdT, rUrU, dUdU or rTrT

<400> SEQUENCE: 5
nnnnnnnnnn nnnnnnnnnn nnnnnnnnnn nnnnnnnnnn nn                42

<210> SEQ ID NO 6
<211> LENGTH: 42

```
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(40)
<223> OTHER INFORMATION: RNA sequence, wherein n is any ribonucleotide -
      where up to 21 n residues are absent
<220> FEATURE:
<221> NAME/KEY: misc_feature
<222> LOCATION: (41)..(42)
<223> OTHER INFORMATION: nn is absent or present; if present, nn is
      dTdT, rUrU, dUdU or rTrT

<400> SEQUENCE: 6
nnnnnnnnnn nnnnnnnnnn nnnnnnnnnn nnnnnnnnnn nn                         42

<210> SEQ ID NO 7
<211> LENGTH: 40
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (20)..(21)
<223> OTHER INFORMATION: uu is rUsrU (5'-uridyl-3'-thiophosphate-5'-
      uridyl-3'-phosphate)

<400> SEQUENCE: 7
agagcgagau gaucuggaau uagagaagau cuacguguua                            40

<210> SEQ ID NO 8
<211> LENGTH: 40
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (20)..(21)
<223> OTHER INFORMATION: uu is rUsrU (5'-uridyl-3'-thiophosphate-5'-
      uridyl-3'-phosphate)

<400> SEQUENCE: 8
agagcgagau gaucuggaau uagagaagau cuacguguua                            40

<210> SEQ ID NO 9
<211> LENGTH: 46
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(20)
<223> OTHER INFORMATION: RNA sequence
<220> FEATURE:
<221> NAME/KEY: misc_feature
<222> LOCATION: (21)..(22)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (23)..(44)
<223> OTHER INFORMATION: RNA sequence
<220> FEATURE:
<221> NAME/KEY: misc_feature
<222> LOCATION: (45)..(46)
<223> OTHER INFORMATION: tt is dTsdT (5'-2'deoxythymidyl-3'-
      thiophosphate-5'-2'deoxythymidyl-3'-phosphate)

<400> SEQUENCE: 9
```
aagagcgaga ugaucuggaa ttuuagagaa gaucuacgug uuagtt                                46

<210> SEQ ID NO 10
<211> LENGTH: 44
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(20)
<223> OTHER INFORMATION: RNA sequence
<220> FEATURE:
<221> NAME/KEY: misc_feature
<222> LOCATION: (21)..(22)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (23)..(42)
<223> OTHER INFORMATION: RNA sequence
<220> FEATURE:
<221> NAME/KEY: misc_feature
<222> LOCATION: (43)..(44)
<223> OTHER INFORMATION: tt is dTsdT (5'-2'deoxythymidyl-3'-
      thiophosphate-5'-2'deoxythymidyl-3'-phosphate)

<400> SEQUENCE: 10
cuaacacgua gaucuucucu ttuuccagau caucucgcuc uutt                                  44

<210> SEQ ID NO 11
<211> LENGTH: 44
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (22)..(42)
<223> OTHER INFORMATION: RNA sequence
<220> FEATURE:
<221> NAME/KEY: misc_feature
<222> LOCATION: (43)..(44)
<223> OTHER INFORMATION: tt is dTsdT (5'-2'deoxythymidyl-3'-
      thiophosphate-5'-2'deoxythymidyl-3'-phosphate)

<400> SEQUENCE: 11
agagcgagau gaucuggaat tuuagagaag aucuacgugu uatt                                  44

<210> SEQ ID NO 12
<211> LENGTH: 42
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:

```
<221> NAME/KEY: misc_feature
<222> LOCATION: (22)..(40)
<223> OTHER INFORMATION: RNA sequence
<220> FEATURE:
<221> NAME/KEY: misc_feature
<222> LOCATION: (41)..(42)
<223> OTHER INFORMATION: tt is dTsdT (5'-2'deoxythymidyl-3'-
      thiophosphate-5'-2'deoxythymidyl-3'-phosphate)

<400> SEQUENCE: 12
uaacacguag aucuucucut tuuccagauc aucucgcucu tt                      42

<210> SEQ ID NO 13
<211> LENGTH: 46
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(20)
<223> OTHER INFORMATION: RNA sequence
<220> FEATURE:
<221> NAME/KEY: misc_feature
<222> LOCATION: (21)..(22)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (23)..(44)
<223> OTHER INFORMATION: RNA sequence
<220> FEATURE:
<221> NAME/KEY: misc_feature
<222> LOCATION: (45)..(46)
<223> OTHER INFORMATION: tt is dTsdT (5'-2'deoxythymidyl-3'-
      thiophosphate-5'-2'deoxythymidyl-3'-phosphate)

<400> SEQUENCE: 13
aagagcgaga ugaucuggaa ttuuagagaa gaucuacgug uuagtt                  46

<210> SEQ ID NO 14
<211> LENGTH: 44
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(20)
<223> OTHER INFORMATION: RNA sequence
<220> FEATURE:
<221> NAME/KEY: misc_feature
<222> LOCATION: (21)..(22)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (23)..(42)
<223> OTHER INFORMATION: RNA sequence
<220> FEATURE:
<221> NAME/KEY: misc_feature
<222> LOCATION: (43)..(44)
<223> OTHER INFORMATION: tt is dTsdT (5'-2'deoxythymidyl-3'-
      thiophosphate-5'-2'deoxythymidyl-3'-phosphate)

<400> SEQUENCE: 14
cuaacacgua gaucuucucu ttuuccagau caucucgcuc uutt                    44

<210> SEQ ID NO 15
<211> LENGTH: 40
<212> TYPE: RNA
<213> ORGANISM: Artificial sequence
<220> FEATURE:
<223> OTHER INFORMATION: Chemically synthesized sequence
```

```
<220> FEATURE:
<221> NAME/KEY: misc_feature
<222> LOCATION: (20)..(21)
<223> OTHER INFORMATION: uu is rUsrU (5'-uridyl-3'-thiophosphate-5'-
      uridyl-3'-phosphate)

<400> SEQUENCE: 15
agagcgagau gaucuggaau uagagaagau cuacguguua                              40

<210> SEQ ID NO 16
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 16
uaacacguag aucuucucuu uccagaucau cucgcucu                                38

<210> SEQ ID NO 17
<211> LENGTH: 44
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(23)
<223> OTHER INFORMATION: ttaa is dTsdTaa (5'-2'deoxythymidyl-3'-
      thiophosphate-5'-2'deoxythymidyl-3'-phosphate-5'-adenyl-3'-
      phosphate-5'-adenyl-3'-phosphate)
<220> FEATURE:
<221> NAME/KEY: misc_feature
<222> LOCATION: (24)..(42)
<223> OTHER INFORMATION: RNA sequence
<220> FEATURE:
<221> NAME/KEY: misc_feature
<222> LOCATION: (43)..(44)
<223> OTHER INFORMATION: tt is dTsdT (5'-2'deoxythymidyl-3'-
      thiophosphate-5'-2'deoxythymidyl-3'-phosphate)

<400> SEQUENCE: 17
agagcgagau gaucuggaat taaagagaag aucuacgugu uatt                         44

<210> SEQ ID NO 18
<211> LENGTH: 44
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (22)..(42)
<223> OTHER INFORMATION: RNA sequence
<220> FEATURE:
<221> NAME/KEY: misc_feature
<222> LOCATION: (43)..(44)
<223> OTHER INFORMATION: tt is dTsdT (5'-2'deoxythymidyl-3'-
      thiophosphate-5'-2'deoxythymidyl-3'-phosphate)

<400> SEQUENCE: 18
```
uaacacguag aucuucucut taauuccaga ucaucucgcu cutt                44

<210> SEQ ID NO 19
<211> LENGTH: 42
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (22)..(40)
<223> OTHER INFORMATION: RNA sequence
<220> FEATURE:
<221> NAME/KEY: misc_feature
<222> LOCATION: (41)..(42)
<223> OTHER INFORMATION: tt is dTsdT (5'-2'deoxythymidyl-3'-
      thiophosphate-5'-2'deoxythymidyl-3'-phosphate)

<400> SEQUENCE: 19
agagcgagau gaucuggaat tagagaagau cuacguguua tt                 42

<210> SEQ ID NO 20
<211> LENGTH: 42
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (22)..(40)
<223> OTHER INFORMATION: RNA sequence
<220> FEATURE:
<221> NAME/KEY: misc_feature
<222> LOCATION: (41)..(42)
<223> OTHER INFORMATION: tt is dTsdT (5'-2'deoxythymidyl-3'-
      thiophosphate-5'-2'deoxythymidyl-3'-phosphate)

<400> SEQUENCE: 20
uaacacguag aucuucucut tuccagauc aucucgcucu tt                  42

<210> SEQ ID NO 21
<211> LENGTH: 46
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(20)
<223> OTHER INFORMATION: RNA sequence
<220> FEATURE:
<221> NAME/KEY: misc_feature
<222> LOCATION: (21)..(24)
<223> OTHER INFORMATION: ttuu is dTsdTuu (5'-2'deoxythymidyl-3'-
      thiophosphate-5'-2'deoxythymidyl-3'-phosphate-5'-uridyl-3'-
      phosphate-5'-uridyl-3'-phosphate)

```
<220> FEATURE:
<221> NAME/KEY: misc_feature
<222> LOCATION: (25)..(44)
<223> OTHER INFORMATION: RNA sequence
<220> FEATURE:
<221> NAME/KEY: misc_feature
<222> LOCATION: (45)..(46)
<223> OTHER INFORMATION: tt is dTsdT (5'-2'deoxythymidyl-3'-
      thiophosphate-5'-2'deoxythymidyl-3'-phosphate)

<400> SEQUENCE: 21
aagagcgaga ugaucuggaa ttuuagagaa gaucuacgug uuagtt            46

<210> SEQ ID NO 22
<211> LENGTH: 46
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(20)
<223> OTHER INFORMATION: RNA sequence
<220> FEATURE:
<221> NAME/KEY: misc_feature
<222> LOCATION: (21)..(24)
<223> OTHER INFORMATION: ttuu is dTsdTuu (5'-2'deoxythymidyl-3'-
      thiophosphate-5'-2'deoxythymidyl-3'-phosphate-5'-uridyl-3'-
      phosphate-5'-uridyl-3'-phosphate)
<220> FEATURE:
<221> NAME/KEY: misc_feature
<222> LOCATION: (25)..(44)
<223> OTHER INFORMATION: RNA sequence
<220> FEATURE:
<221> NAME/KEY: misc_feature
<222> LOCATION: (45)..(46)
<223> OTHER INFORMATION: tt is dTsdT (5'-2'deoxythymidyl-3'-
      thiophosphate-5'-2'deoxythymidyl-3'-phosphate)

<400> SEQUENCE: 22
cuaacacgua gaucuucucu ttuuuuccag aucaucucgc ucuutt            46

<210> SEQ ID NO 23
<211> LENGTH: 48
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (22)..(46)
<223> OTHER INFORMATION: RNA sequence
<220> FEATURE:
<221> NAME/KEY: misc_feature
<222> LOCATION: (23)..(24)
<223> OTHER INFORMATION: Residues 23 and 24 are linked together by HEG-
      linker (hexaethylenglycol)
<220> FEATURE:
<221> NAME/KEY: misc_feature
<222> LOCATION: (47)..(48)
<223> OTHER INFORMATION: tt is dTsdT (5'-2'deoxythymidyl-3'-
      thiophosphate-5'-2'deoxythymidyl-3'-phosphate)

<400> SEQUENCE: 23
agagcgagau gaucuggaat taauuaaaga gaagaucuac guguuatt          48
```

```
<210> SEQ ID NO 24
<211> LENGTH: 48
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT (5'-2'deoxythymidyl-3'-
      thiophosphate-5'-2'deoxythymidyl-3'-phosphate)
<220> FEATURE:
<221> NAME/KEY: misc_feature
<222> LOCATION: (22)..(46)
<223> OTHER INFORMATION: RNA sequence
<220> FEATURE:
<221> NAME/KEY: misc_feature
<222> LOCATION: (23)..(24)
<223> OTHER INFORMATION: Residues 23 and 24 are linked together by HEG-
      linker (hexaethylenglycol)
<220> FEATURE:
<221> NAME/KEY: misc_feature
<222> LOCATION: (47)..(48)
<223> OTHER INFORMATION: tt is dTsdT (5'-2'deoxythymidyl-3'-
      thiophosphate-5'-2'deoxythymidyl-3'-phosphate)

<400> SEQUENCE: 24
cccaagcaau ggaugauuut taauuaauuc cagaucaucu cgcucutt                 48

<210> SEQ ID NO 25
<211> LENGTH: 48
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)
<220> FEATURE:
<221> NAME/KEY: misc_feature
<222> LOCATION: (22)..(46)
<223> OTHER INFORMATION: RNA sequence
<220> FEATURE:
<221> NAME/KEY: misc_feature
<222> LOCATION: (23)..(24)
<223> OTHER INFORMATION: Residues 23 and 24 are linked together by
      HEG-linker (hexaethylenglycol)
<220> FEATURE:
<221> NAME/KEY: misc_feature
<222> LOCATION: (47)..(48)
<223> OTHER INFORMATION: tt is dTsdT
      (5'-2'deoxythymidyl-3'-thiophosphate-5'-2'deoxythymidyl-3'-
      phosphate)

<400> SEQUENCE: 25
uaacacguag aucuucucut taauuaaaaa ucauccauug cuugggtt                 48

<210> SEQ ID NO 26
<211> LENGTH: 52
<212> TYPE: DNA
<213> ORGANISM: Artificial sequence
<220> FEATURE:
<223> OTHER INFORMATION: Chemically synthesized sequence
<220> FEATURE:
```

```
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)
<220> FEATURE:
<221> NAME/KEY: misc_feature
<222> LOCATION: (22)..(23)
<223> OTHER INFORMATION: RNA sequence
<220> FEATURE:
<221> NAME/KEY: misc_feature
<222> LOCATION: (24)..(27)
<223> OTHER INFORMATION: TTTT-linker (poly(5'-2'deoxythymidyl-3'-
      phosphate))
<220> FEATURE:
<221> NAME/KEY: misc_feature
<222> LOCATION: (28)..(50)
<223> OTHER INFORMATION: RNA sequence
<220> FEATURE:
<221> NAME/KEY: misc_feature
<222> LOCATION: (51)..(52)
<223> OTHER INFORMATION: tt is dTsdT
      (5'-2'deoxythymidyl-3'-thiophosphate-5'-2'deoxythymidyl-3'-
      phosphate)

<400> SEQUENCE: 26
agagcgagau gaucuggaat taattttuua aagagaagau cuacguguua tt          52

<210> SEQ ID NO 27
<211> LENGTH: 52
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)
<220> FEATURE:
<221> NAME/KEY: misc_feature
<222> LOCATION: (22)..(23)
<223> OTHER INFORMATION: RNA sequence
<220> FEATURE:
<221> NAME/KEY: misc_feature
<222> LOCATION: (24)..(27)
<223> OTHER INFORMATION: TTTT-linker (poly(5'-2'deoxythymidyl-3'-
      phosphate))
<220> FEATURE:
<221> NAME/KEY: misc_feature
<222> LOCATION: (28)..(50)
<223> OTHER INFORMATION: RNA sequence
<220> FEATURE:
<221> NAME/KEY: misc_feature
<222> LOCATION: (51)..(52)
<223> OTHER INFORMATION: tt is dTsdT
      (5'-2'deoxythymidyl-3'-thiophosphate-5'-2'deoxythymidyl-3'-
      phosphate)

<400> SEQUENCE: 27
cccaagcaau ggaugauuut taattttuua auuccagauc aucucgcucu tt          52

<210> SEQ ID NO 28
<211> LENGTH: 52
<212> TYPE: DNA
<213> ORGANISM: Artificial sequence
<220> FEATURE:
```

```
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)
<220> FEATURE:
<221> NAME/KEY: misc_feature
<222> LOCATION: (22)..(23)
<223> OTHER INFORMATION: RNA sequence
<220> FEATURE:
<221> NAME/KEY: misc_feature
<222> LOCATION: (24)..(27)
<223> OTHER INFORMATION: TTTT-linker (poly(5'-2'deoxythymidyl-3'-
      phosphate)
<220> FEATURE:
<221> NAME/KEY: misc_feature
<222> LOCATION: (28)..(50)
<223> OTHER INFORMATION: RNA sequence
<220> FEATURE:
<221> NAME/KEY: misc_feature
<222> LOCATION: (51)..(52)
<223> OTHER INFORMATION: tt is dTsdT
      (5'-2'deoxythymidyl-3'-thiophosphate-5'-2'deoxythymidyl-3'-
      phosphate)

<400> SEQUENCE: 28
uaacacguag aucuucucut taattttuua aaaucaucc auugcuuggg tt            52

<210> SEQ ID NO 29
<211> LENGTH: 47
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (20)..(28)
<223> OTHER INFORMATION: RNA-linker (poly(5'-adenyl-3'-phosphate))

<400> SEQUENCE: 29
agagcgagau gaucuggaaa aaaaaaaag agaagaucua cguguua                 47

<210> SEQ ID NO 30
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 30
uaacacguag aucuucucuu uccagaucau cucgcucu                          38

<210> SEQ ID NO 31
<211> LENGTH: 47
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(28)
<223> OTHER INFORMATION: DNA-linker (poly(5'-2'deoxythymidyl-3'-
      phosphate))
<220> FEATURE:
```

```
<221> NAME/KEY: misc_feature
<222> LOCATION: (29)..(47)
<223> OTHER INFORMATION: RNA sequence

<400> SEQUENCE: 31
agagcgagau gaucuggaat tttttttag agaagaucua cguguua                    47

<210> SEQ ID NO 32
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 32
uaacacguag aucuucucuu uccagaucau cucgcucu                             38

<210> SEQ ID NO 33
<211> LENGTH: 38
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (19)..(20)
<223> OTHER INFORMATION: Residues 19 and 20 are linked together by a
      disulfide bond.

<400> SEQUENCE: 33
agagcgagau gaucuggaaa gagaagaucu acguguua                             38

<210> SEQ ID NO 34
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 34
uaacacguag aucuucucuu uccagaucau cucgcucu                             38

<210> SEQ ID NO 35
<211> LENGTH: 19
<212> TYPE: RNA
<213> ORGANISM: Artificial sequence
<220> FEATURE:
<223> OTHER INFORMATION: Chemically synthesized sequence

<400> SEQUENCE: 35
agagcgagau gaucuggaa                                                  19

<210> SEQ ID NO 36
<211> LENGTH: 5
<212> TYPE: PRT
<213> ORGANISM: Artificial sequence
<220> FEATURE:
<223> OTHER INFORMATION: Chemically synthesized sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid

<400> SEQUENCE: 36

Xaa Gly Phe Gly Xaa
```

```
<210> SEQ ID NO 37
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 37
uaacacguag aucuucucuu uccagaucau cucgcucu                                  38

<210> SEQ ID NO 38
<211> LENGTH: 21
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
     (5'-2'deoxythymidyl-3'-thiophosphate-5'-2'deoxythymidyl-3'-
     phosphate)

<400> SEQUENCE: 38
agagcgagau gaucuggaat t                                                   21

<210> SEQ ID NO 39
<211> LENGTH: 21
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
     (5'-2'deoxythymidyl-3'-thiophosphate-5'-2'deoxythymidyl-3'-
     phosphate)

<400> SEQUENCE: 39
uuccagauca ucucgcucut t                                                   21

<210> SEQ ID NO 40
<211> LENGTH: 21
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
     (5'-2'deoxythymidyl-3'-thiophosphate-5'-2'deoxythymidyl-3'-
     phosphate)

<400> SEQUENCE: 40
agagaagauc uacguguuat t                                                   21
```

```
<210> SEQ ID NO 41
<211> LENGTH: 21
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)

<400> SEQUENCE: 41
uaacacguag aucuucucut t                                             21

<210> SEQ ID NO 42
<211> LENGTH: 21
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)

<400> SEQUENCE: 42
cccaagcaau ggaugauuut t                                             21

<210> SEQ ID NO 43
<211> LENGTH: 21
<212> TYPE: DNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (1)..(19)
<223> OTHER INFORMATION: RNA sequence
<220> FEATURE:
<221> NAME/KEY: misc_feature
<222> LOCATION: (20)..(21)
<223> OTHER INFORMATION: tt is dTsdT
      (5'-2'deoxythymidyl-3'-thiophosphate-5'-2'deoxythymidyl-3'-
      phosphate)

<400> SEQUENCE: 43
aaaucaucca uugcuugggt t                                             21

<210> SEQ ID NO 44
<211> LENGTH: 40
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (20)..(21)
<223> OTHER INFORMATION: uu is rUsrU (5'-uridyl-3'-thiophosphate-5'-
      uridyl-3'-phosphate)

<400> SEQUENCE: 44
```

```
agagcgagau gaucuggaau uagagaagau cuacguguua                    40
```

<210> SEQ ID NO 45
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 45

```
uaacacguag aucuucucuu uccagaucau cucgcucu                      38
```

<210> SEQ ID NO 46
<211> LENGTH: 47
<212> TYPE: RNA
<213> ORGANISM: Artificial sequence
<220> FEATURE:
<223> OTHER INFORMATION: Chemically synthesized sequence

<400> SEQUENCE: 46

```
agagcgagau gaucuggaaa aaaaaaaaag agaagaucua cguguua            47
```

<210> SEQ ID NO 47
<211> LENGTH: 47
<212> TYPE: RNA
<213> ORGANISM: Artificial sequence
<220> FEATURE:
<223> OTHER INFORMATION: Chemically synthesized sequence

<400> SEQUENCE: 47

```
uaacacguag aucuucucuu uuuuuuuuuu ccagaucauc ucgcucu            47
```

<210> SEQ ID NO 48
<211> LENGTH: 47
<212> TYPE: RNA
<213> ORGANISM: Artificial sequence
<220> FEATURE:
<223> OTHER INFORMATION: Chemically synthesized sequence

<400> SEQUENCE: 48

```
agagcgagau gaucuggaaa aaaaaaaaag agaagaucua cguguua            47
```

<210> SEQ ID NO 49
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 49

```
uaacacguag aucuucucuu uccagaucau cucgcucu                      38
```

<210> SEQ ID NO 50
<211> LENGTH: 47
<212> TYPE: RNA
<213> ORGANISM: Artificial sequence
<220> FEATURE:
<223> OTHER INFORMATION: Chemically synthesized sequence

<400> SEQUENCE: 50

```
agagcgagau gaucuggaac ucucucucag agaagaucua cguguua            47
```

<210> SEQ ID NO 51
<211> LENGTH: 38
<212> TYPE: RNA
<213> ORGANISM: Artificial sequence

```
<220> FEATURE:
<223> OTHER INFORMATION: Chemically synthesized sequence

<400> SEQUENCE: 51
uaacacguag aucuucucuu uccagaucau cucgcucu                              38

<210> SEQ ID NO 52
<211> LENGTH: 38
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (19)..(20)
<223> OTHER INFORMATION: Residues 19 and 20 are together linked by a
      disulfide bond

<400> SEQUENCE: 52
agagcgagau gaucuggaaa gagaagaucu acguguua                              38

<210> SEQ ID NO 53
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 53
uaacacguag aucuucucuu uccagaucau cucgcucu                              38

<210> SEQ ID NO 54
<211> LENGTH: 38
<212> TYPE: RNA
<213> ORGANISM: Artificial sequence
<220> FEATURE:
<223> OTHER INFORMATION: Chemically synthesized sequence

<400> SEQUENCE: 54
agagcgagau gaucuggaaa gagaagaucu acguguua                              38

<210> SEQ ID NO 55
<211> LENGTH: 40
<212> TYPE: RNA
<213> ORGANISM: Artificial sequence
<220> FEATURE:
<223> OTHER INFORMATION: Chemically synthesized sequence
<220> FEATURE:
<221> NAME/KEY: misc_feature
<222> LOCATION: (21)..(22)
<223> OTHER INFORMATION: uu is rUsrU (5'-uridyl-3'-thiophosphate-5'-
      uridyl-3'-phosphate)

<400> SEQUENCE: 55
uaacacguag aucuucucuu uuccagauc aucucgcucu                             40

<210> SEQ ID NO 56
<211> LENGTH: 19
<212> TYPE: RNA
<213> ORGANISM: Artificial sequence
<220> FEATURE:
<223> OTHER INFORMATION: Chemically synthesized sequence

<400> SEQUENCE: 56
agagaagauc uacguguua                                                   19
```